US008168397B2

(12) United States Patent
Charlton et al.

(10) Patent No.: US 8,168,397 B2
(45) Date of Patent: May 1, 2012

(54) METHODS FOR THE TREATMENT OF AN INFECTIOUS BACTERIAL DISEASE WITH AN ANTI-LACTONE OR LACTONE DERIVED SIGNAL MOLECULES ANTIBODY

(75) Inventors: Keith Alan Charlton, Aberdeen (GB); Andrew Justin Radcliffe Porter, Aberdeen (GB)

(73) Assignee: Haptogen Ltd., Aberdeen (GB)

( * ) Notice: Subject to any disclaimer, the term of this patent is extended or adjusted under 35 U.S.C. 154(b) by 0 days.

(21) Appl. No.: 12/791,927

(22) Filed: Jun. 2, 2010

(65) Prior Publication Data

US 2010/0303831 A1     Dec. 2, 2010

Related U.S. Application Data

(63) Continuation of application No. 10/524,082, filed as application No. PCT/GB03/03529 on Aug. 13, 2003, now Pat. No. 7,812,134.

(30) Foreign Application Priority Data

Aug. 13, 2002  (GB) ................................ 0218951.2
Mar. 24, 2003  (GB) ................................ 0306783.2

(51) Int. Cl.
*G01N 33/53*     (2006.01)
*G01N 33/554*    (2006.01)
(52) U.S. Cl. ......................... 435/7.1; 435/7.2; 435/7.32
(58) Field of Classification Search ........................ None
See application file for complete search history.

(56) References Cited

U.S. PATENT DOCUMENTS

| | | | |
|---|---|---|---|
| 5,254,671 A | 10/1993 | Chang | |
| 6,090,388 A * | 7/2000 | Wang | 424/185.1 |
| 6,395,282 B1 | 5/2002 | Kende et al. | |
| 6,703,513 B1 | 3/2004 | Quay | |
| 6,713,059 B2 | 3/2004 | Kende et al. | |
| 7,384,639 B2 | 6/2008 | Kende et al. | |
| 7,812,134 B2 * | 10/2010 | Charlton et al. | 530/387.3 |
| 2003/0095985 A1 | 5/2003 | Kende et al. | |
| 2004/0147592 A1 | 7/2004 | Quay | |
| 2006/0165704 A1 | 7/2006 | Charlton et al. | |
| 2007/0218058 A1 | 9/2007 | Charlton et al. | |

FOREIGN PATENT DOCUMENTS

| | | |
|---|---|---|
| JP | 2000186042 A1 | 7/2000 |
| JP | 2002-514092 A1 | 5/2002 |
| WO | 98/58075 A2 | 12/1998 |
| WO | 99/27786 | 6/1999 |
| WO | 01/94543 | 12/2001 |
| WO | 2002/018342 A2 | 3/2002 |
| WO | 2004/014423 A1 | 2/2004 |

OTHER PUBLICATIONS

Erickson, D. L., et al., *Pseudomonas aeruginosa* quorum-sensing systems may control virulence factor expression in the lungs of patients with cystic fibrosis, Infection and Immunity, Apr. 2002;70(4):1783-1790.
European Search Report mailed Dec. 14, 2010.
McElhiney, J., et al., Rapid isolation of a single-chain antibody against the cyanobacterial toxin microcystin-LR by phage display and its use in the immunoaffinity concentration of microcystins from water, Appl Environ Microbiol. Nov. 2002;68(11):5288-95.
Non-final Office Action dated Jun. 17, 2010 in co-pending U.S. Appl. No. 11/568,673.
Final Office Action dated Dec. 6, 2010 in co-pending U.S. Appl. No. 11/568,671.
Non-Final Office Action dated Jul. 13, 2009 in co-pending U.S. Appl. No. 10/599,355.
Final Office Action dated Jan. 19, 2010 in co-pending U.S. Appl. No. 10/599,355.
D'Argenio, et al., Autolysis and autoaggregation in *Pseudomonas aeruginosa* colony morphology mutants, Journal of Bacteriology, 2002;184(23):6481-6489.
McGrath, et al., Dueling quorum sensing systems in *Pseudomonas aeruginosa* control the production of the *Pseudomonas quinolone* signal (PQS), FEMS Microbiology Letters, 2004;230(1):27-34.
Charlton, K., et al., The isolation of super-sensitive anti-hapten antibodies from combinatorial antibody libraries derived from sheep, Biosens Bioelectron., Dec. 2001;16(9-12):639-46.
Chen, X., et al., Structural identification of a bacterial quorum-sensing signal containing boron, Nature, Jan. 31, 2002;415(6871):545-9.
Dong, Y. H., et al., Quenching quorum-sensing-dependent bacterial infection by an N-acyl homoserine lactonase, Nature, Jun. 14, 2001;411(6839):813-7.
Finch, R. G., et al., Quorum sensing: a novel target for anti-infective therapy, J Antimicrob Chemother, Nov. 1998;42(5):569-71.
International Search Report dated Dec. 12, 2003 for International Application No. PCT/GB03/03529.
Mayville, P., et al, Structure-activity analysis of synthetic autoinducing thiolactone peptides from *Staphylococcus aureus* responsible for virulence, Proc Natl Acad Sci U S A., Feb. 16, 1999;96(4):1218-23.
Moghaddam, A., et al., Identification of scFv antibody fragments that specifically recognise the heroin metabolite 6-monoacetylmorphine but not morphine, J Immunol Methods., Sep. 2003;280(1-2):139-55.
Moghaddam, A., et al., Selection and characterisation of recombinant single-chain antibodies to the hapten Aflatoxin-B1 from naive recombinant antibody libraries, J Immunol Methods., Aug. 1, 2001;254(1-2):169-81.

(Continued)

*Primary Examiner* — Albert Navarro
(74) *Attorney, Agent, or Firm* — Pfizer Inc.; John L. Miller; Raquel M. Alvarez

(57) ABSTRACT

The present invention relates to methods for the control of virulence of infectious bacteria by modulating the extra-cellular concentration of bacterial cell signalling molecules. Derivatives of cell signalling molecules are conjugated to suitable carrier proteins and used to isolate high affinity receptors recognizing the native signal molecule(s). By binding to signalling molecules, the receptors reduce and maintain extra-cellular concentrations of signal molecules below the threshold level that would otherwise result in certain opportunistic pathogens adopting a virulent form, and can transform virulent organisms to non-virulent states. These receptors have applications for the treatment of individuals with susceptibility to infection, the treatment of patients with existing infections, in disease monitoring and management, and in related applications where the host for infection is an animal or plant.

14 Claims, 12 Drawing Sheets

OTHER PUBLICATIONS

Reverchon, S., et al., New synthetic analogues of N-acyl homoserine lactones as agonists or antagonists of transcriptional regulators involved in bacterial quorum sensing, Bioorg Med Chem Lett., Apr. 22, 2002;12(8):1153-7.

Wu, H., et al., Detection of N-acylhomoserine lactones in lung tissues of mice infected with *Pseudomonas aeruginosa*, Microbiology, Oct. 2000;146 ( Pt 10):2481-93.

McCafferty, J., et al., Phage antibodies: filamentous phage displaying antibody variable domains, Nature, Dec. 6, 1990;348(6301):552-4.

Hartman, et al., Quorum sensing: potential means for treating gram-negative infections?, The Lancet 1998;351:848-849.

Notice of Allowance dated Jun. 7, 2010 in co-pending U.S. Appl. No. 10/524,082.

Advisory Action dated Dec. 10, 2008 in co-pending U.S. Appl. No. 10/524,082.

Final Office Action dated Sep. 8, 2008 in co-pending U.S. Appl. No. 10/524,082.

Non-Final Office Action dated Jan. 24, 2008 in co-pending U.S. Appl. No. 10/724.082.

Non-Final Office Action dated Apr. 24, 2009 in co-pending U.S. Appl. No. 10/524,082.

Final Office Action dated Dec. 2, 2009 in co-pending U.S. Appl. No. 10/524,082.

Non-Final Office Action dated Jun. 27, 2011 in U.S. Appl. No. 12/837,588.

Ikeda, Otsukasa, et al., The Control Methods of Quorum Sensing in Gram Negative Bacteria, Utsunomiya University, Department of Applied Chemistry, 2003.

Final Office Action dated Nov. 8, 2011 in co-pending U.S. Appl. No. 12/837,588.

* cited by examiner i) Acyl-homoserine lactone, e.g. BHL (n=0), dDHL (n=8), tDHL (n=10)

ii) 3-oxo-homoserine lactone, e.g. OHHL (n=2), OdDHL (n=8)

iii) 3-hydroxy-homoserine lactone, e.g. HBHL (n=0)

Pro AI-2

Auto Inducer-2 (AI-2)

Pro-AI-2-reactive hapten

FIG. 2
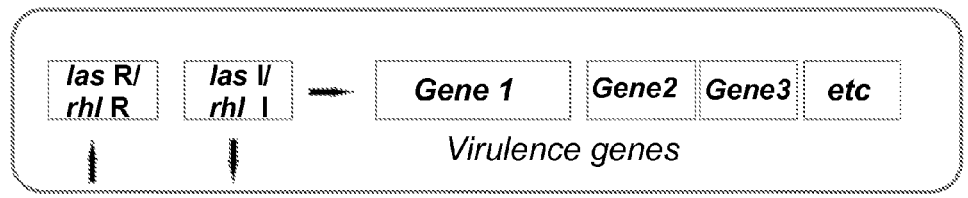
regulation
| las I/ rhl I | Produce long chain (las I) and short chain (rhl I) HSLs |
| las R/ rhl R | Respond to long chain (las R) and short chain (rhl R) HSLs |
FIG. 3
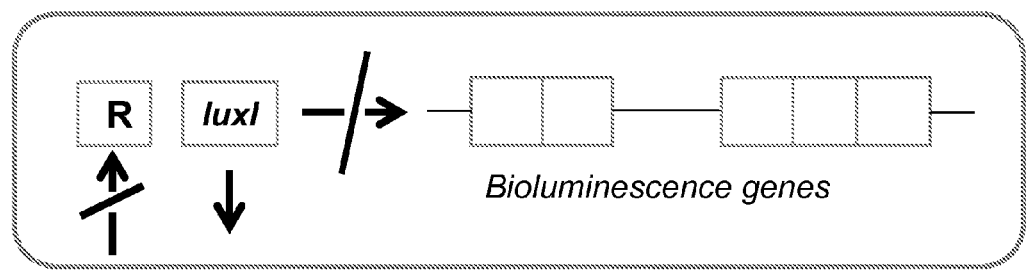
Anti-HSL antibodies stop gene expression by preventing HSL from binding to receptors
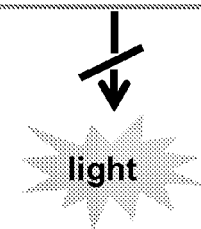

FIG. 10

Table 1

| Organism | Regulatory proteins | Signal molecule | Phenotype |
|---|---|---|---|
| *Aeromonas hydrophila* | AhyI/AhyR | BHL, HHL | serine protease, metalloprotease |
| *Aeromonas salmonicida* | AsaI/AsaR | BHL, HHL | ? |
| *Agrobacterium tumefaciens* | TraI/TraR | HHL, OOHL | conjugation |
| *Burkholderia cepacia* | CepI/CepR | OHL | ornibactin, siderophores, exoprotease |
| *Chromobacterium violaceum* | CviI/CviR | HHL | antibiotics, violacein, exoenzymes, cyanide |
| *Erwinia carotovora* | CarI/CarR ExpI/ExpR | OHHL +? | carbapenem antibiotic exoenzymes |
| *Erwinia chrysanthemi* | ExpI/ExpR | OHHL, HHL | pectate lyase |
| *Escherichia coli* | ?/SdiR LuxS/? | ? AI-2 | cell division ? |
| *Pantoea stewartii* | EsaI/EsaR | OHHL | Exopolysaccharide |
| *Pseudomonas aeruginosa* | LasI/LasR RhlI/RhlR | OdDHL, OHHL, OOHL BHL, HHL | Virulence factors inc: alkaline protease, elastase exotoxin A Chitinase, pyocyanin, rhamnolipid |
| *Pseudomonas aureofaciens* | PhzI/PhzR | BHL, HHL | Phenazine antibiotic |
| *Pseudomonas fluorescens* | PhzI/PhzR | OHL, HHHL, HOHL, HDHL | Phenazine antibiotic |
| *Ralstonia solanacearum* | SolI/SolR | HHL, OHL | ? (aidA) |
| *Rhizobium leguminosarum* | RhiI/RhiR | HHL, OHL | Nodulation |
| *Rhodobacter sphaeroides* | CerI/CerR | ? | Community escape EPS expressiom |
| *Serratia liquifaciens* | SwrI/? | BHL, HHL | Swarming, phospholipase |
| *Vibrio anguillarum* | VanI/VanR | ODHL | ? |
| *Vibrio fischeri* | LuxI/LuxR AinS/AinR | OHHL, HHL OHL | Bioluminescence |
| *Vibrio harveyi* | LuxI/LuxR LuxPQ/LuxS | HBHL AI-2 | bioluminescemce |
| *Xenorhabdus nematophilus* | ? | HBHL | Virulence factors |
| *Yersinia enterocolitica* | YcnI.YcnR | HHL, OHHL | ? |
| *Yersinia pestis* | YpeI/YeR | HHL, OHHL | Pathogenicity |
| *Yersinia pseudotuberculosis* | YpsI/YpsR YtbI/YtbR | HHL, OHHL OHL | Flagella production ? |
| *Bascillus anthracis* | ? | AI-2 | Virulence factors |

FIG. 11A
Table 2.

| scAb | dDHL-COOH | tDHL | OHHL | dDHL-BSA | Paraquat |
|------|-----------|------|------|----------|----------|
| G3G2 | 11 μM | 21 μM | 17 mM | 0.28 μM | N/D |
| G3B12 | 4 μM | 5 μM | 2 mM | 0.32 μM | N/D |

N/D indicates that no $IC_{50}$ value could be determined.

FIG. 11B
Table 3.

| scAb | ka (mol $l^{-1}$ $s^{-1}$) | kd ($s^{-1}$) | KA (mol/l) | KD (nM) |
|------|------|------|------|------|
| G3G2 | $4.19 \times 10^4$ | $1.43 \times 10^{-3}$ | $2.93 \times 10^7$ | 34.1 |
| G3B12 | $3.93 \times 10^4$ | $1.56 \times 10^{-3}$ | $2.52 \times 10^7$ | 39.7 |

FIG. 11C
Table 4.

| scAb | BHL | dDHL | tDHL | OHHL | Paraquat |
|------|-----|------|------|------|----------|
| G3B12 | 17 mM | 1.4 mM | 4.5 mM | 10 mM | N/D |
| L1-A7 (G3B12) | 1.25 mM (× 13.6) | 40 μM (× 35) | - | - | N/D |
| L1-B7 (G3B12) | - | 130 μM (× 10.8) | - | - | N/D |
| L1-C11 (G3B12) | - | 200 μM (× 7) | - | - | N/D |
| G12 (G3B12) | 3 mM (× 5.7) | - | 0.6 mM (× 7.5) | 5 mM (× 2) | N/D |

FIG. 12

Table 5.

|  | High Optical density | | | | | Low density | |
|---|---|---|---|---|---|---|---|
| Inc Days | PBS Control | Control scAb | G3H5 | G3B12 | G3H3 | PBS Control | 3 scAb mixture |
| 1 | 100 | 100 | 100 | 100 | 100 | 100 | 100 |
| 2 | 100 | 100 | 100 | 100 | 100 | 100 | 82 |
| 3 | 100 | 95 | 70 | 68 | 84 | 100 | 75 |
| 4 | 100 | 100 | 58 | 52 | 65 | 100 | 65 |
| 5 | 100 | 95 | 52 | 47 | 49 | 100 | 56 |

METHODS FOR THE TREATMENT OF AN INFECTIOUS BACTERIAL DISEASE WITH AN ANTI-LACTONE OR LACTONE DERIVED SIGNAL MOLECULES ANTIBODY

FIELDS OF THE INVENTION

The present invention relates to methods for controlling and treating bacterial infections in patients. The methods of the invention are applicable to most, if not all gram negative and grain-positive bacterial infections. The invention provides for the application of therapies based upon, in the preferred embodiment, immunoglobulin or immunoglobulin-like receptor -molecules that have affinity and specificity for signalling molecules involved in the processes of bacterial cell to cell communication. By binding to such molecules, the receptors can be used to diagnose the presence of bacteria or to assess the disease state of patients, and can further be used to control concentrations of molecules involved in inducing a virulent state in opportunistic and other pathogens.

BACKGROUND OF THE INVENTION

One of the major causes of mortality and morbidity amongst patients undergoing treatment in hospitals today is due to hospital acquired infection. Susceptibility to such infection can be as a result of the primary illness for which the patient was admitted, of immuno-suppressive treatment regimes, or as a consequence of injury resulting in serious skin damage, such as bums. The bacterium to which the highest proportion of cases is attributed is *Pseudomonas aeruginosa*. It is the epitome of an opportunistic pathogen of humans. The bacterium almost never infects uncompromised tissues, yet there is hardly any tissue that it cannot infect, if the tissue defences are compromised in some manner. Although accounting for a relatively small number of species, it poses a serious threat to human health and is used hereafter as a representative example of an infectious bacterium, and does not in any way limit the scope or extent of the present invention.

*Ps. aeruginosa* is an opportunistic pathogen that causes urinary tract infections, respiratory system infections, dermatitis, soft tissue infections, bacteraemia and a variety of systemic infections, particularly in victims of severe bums, and in cancer and AIDS patients who are immunosuppressed. Respiratory infections caused by *Ps. aeruginosa* occur almost exclusively in individuals with a compromised lower respiratory tract or a compromised systemic defence mechanism. Primary pneumonia occurs in patients with chronic lung disease and congestive heart failure. Bacteraemic pneumonia commonly occurs in neutropenic cancer patients undergoing chemotherapy. Lower respiratory tract colonisation of cystic fibrosis patients by mucoid strains of *Ps. aeruginosa* is common and difficult, if not impossible, to treat.

It causes bacteraemia primarily in immuno-compromised patients. Predisposing conditions include haematologic malignancies, immuno-deficiency relating to AIDS, neutropenia, diabetes mellitus, and severe burns. Most *Pseudomonas* bacteraemia is acquired in hospitals and nursing homes where it accounts for about 25 percent of all hospital acquired gram-negative bacteraemias.

The bacterium is notorious for its natural resistant to many antibiotics due to the permeability barrier afforded by its outer membrane LPS and is, therefore, a particularly dangerous and dreaded pathogen. Also, its tendency to colonise surfaces in a biofilm form makes the cells impervious to therapeutic concentrations of antibiotics. Since its natural habitat is the soil, living in association with the bacilli, actinomycetes and moulds, it has developed resistance to a variety of their naturally occurring antibiotics. Moreover, *Pseudomonas* spp. maintain antibiotic resistance plasmids, both Resistance factors (R-factors) and Resistance Transfer Factors (RTFs), and arc able to transfer these genes by means of the bacterial processes of transduction and conjugation. Only a few antibiotics are effective against *Pseudomonas*, including fluoroquinolone, gentamicin and imipenem, and even these antibiotics are not effective against all strains. Combinations of gentamicin and carbenicillin are reportedly effective in patients with acute *Ps. aeruginosa* infections. The futility of treating *Pseudomonas* infections with antibiotics is most dramatically illustrated in cystic fibrosis patients, virtually all of whom eventually become infected with a strain that is so resistant it cannot be treated. Because of antibiotic resistance, susceptibility testing of clinical isolates is mandatory.

*Ps. aeruginosa* can usually be isolated from soil and water, as well as the surfaces of plants and animals. It is found throughout the world, wherever these habitats occur, so it is quite a "cosmopolitan" bacterium. It is sometimes present as part of the normal flora of humans, although the prevalence of colonisation of healthy individuals outside the hospital is relatively low (estimates range from 0 to 24 percent depending on the anatomical locale). In hospitals it is known to colonise food, sinks, taps, mops, respiratory equipment surgical instruments. Although colonisation usually precedes infections by *Ps. aeruginosa*, the exact source and mode of transmission of the pathogen are often unclear because of its ubiquitous presence in the environment. Amongst intensive care patients in whom infection is suspected on clinical grounds, as many as 50% have no identifiable source for infection. Currently 1,400 deaths worldwide are caused each day by *Ps. aeruginosa* in intensive care units (ICU's), making it the No 1 killer.

*Ps. aeruginosa* is primarily a nosocomial pathogen. According to the CDC, the overall incidence of *Ps. aeruginosa* infections in US hospitals averages about 0.4 percent (4 per 1000 discharges), and the bacterium is the fourth most commonly isolated nosocomial pathogen accounting for 10.1% of all hospital-acquired infections. Globally it is responsible for 16% of nosocomial pneumonia cases, 12% of acquired urinary tract infections, 8% of surgical wound infections and 10% of bloodstream infections. Immuno-compromised patients such as neutropenic cancer and bone marrow transplant patients are susceptible to opportunistic *Ps. aeruginosa* infection, leading to 30% reported deaths. It is also responsible for 38% of ventilator-associated pneumonias and 50% of deaths amongst AIDS patients. In burns cases *Ps. aeruginosa* infections have declined in recent years due to improved treatment and dietary changes. Mortality rates however remain high, accounting for 60% all deaths due to secondary infection of burns patients.

One reason for the versatility of *Ps. aeruginosa* is that it produces a diverse battery of virulence determinants including elastase, LasA protease, alkaline protease, rhamnolipids, type IV pilus-mediated twitching motility, pyoverdin (Williams et al., 1996, Stintzi et al., 1998, Glessner et al., 1999), pyocyanin (Brint & Ohman, 1995, Reimmann et al., 1997) and the cytotoxic lectins PA-I and PA-II (Winzer et al., 2000). It is now known that many of these virulence determinants are regulated at the genetic level in a cell density-dependent manner through quorum sensing. *Ps. aeruginosa* possesses at least two quorum sensing systems, namely the las and rhl (vsm) systems which comprise of the LuxRI homologues LasRI (Gambello & Iglewski, 1991) and RhlRI (VsmRI)

(Latifi et al., 1995) respectively (FIG. 2). LasI directs the synthesis of 3-oxo-C12-HSL (Passador et al., 1993, Pearson et al., 1994) whereas RhlI directs the synthesis of C4-HSL (Winson et al., 1995). The las and the rhl systems are thought to exist in a hierarchy where the las system exerts transcriptional control over RhlR (Williams et al., 1996, Pesci et al., 1997). The transcriptional activator LasR functions in conjunction with 3-oxo-C12-HSL to regulate the expression of the genes encoding for the virulence determinants elastase, LasA protease, alkaline protease and exotoxin A (Gambello & Iglewski, 1991, Toder et al., 1991, Gambello et al., 1993, Pearson et al., 1994) as well as lasI. Elastase is able to cleave collagen, IgG and IgA antibodies, complement, and facilitates bacterial adhesion onto lung mucosa. In combination with alkaline protease it also causes inactivation of gamma Interferon (INF) and Tumour Necrosis Factor (TNF). LasI directs the synthesis of 3-oxo-C12-HSL which together with LasR, binds to the lasI promoter and creates a positive feedback system. The RhlR transcriptional activator, along with its cognate AHL (C4-HSL), regulates the expression of rhlAB (rhamnolipid), lasB, aprA, RpoS, cyanide, pyocyanin and the lectins PA-I and PA-II (Ochsner et al., 1994, Brint & Ohman, 1995, Latifi et al., 1995, Pearson et al., 1995, Winson et al., 1995, Latifi et al., 1996, Winzer et al., 2000). These exist in a hierarchical manner where by the LasR/3-oxo-C12-HSL regulates rhlR (Latifi et al., 1996, Pesci et al., 1997) and consequently both systems are required for the regulation of all the above virulence determinants.

A number of different approaches are being actively pursued to develop therapeutics for the treatment or prevention of Ps. aeruginosa infection. Some are intended to be broad ranging while others are directed at specific types of Pseudomonas infection. Those that follow traditional routes include the development of vaccines such as that described in U.S. Pat. No. 6,309,651, and a new antibiotic drug (SLIT) that is hoped will be effective against gram-negative bacteria in general but is designed primarily to act against Ps. aeruginosa and is administered by aerosol inhalation. A further observation under investigation is that the antibiotic erythromycin administered at sub-optimal growth inhibitory concentrations simultaneously suppresses the production of Ps. aeruginosa haemagglutinins, haemolysin, proteases and homoserine lactones (HSLs), and may be applicable for the treatment of persistent Ps. aeruginosa infection. Cream formulations containing amphipathic peptides are also being examined as a possible means of preventing infection of burns or other serious skin wounds. U.S. Pat. No. 6,309,651 also teaches that antibodies against the PcrV virulence protein of Ps. aeruginosa may afford protection against infection.

There is also some interest in the modulation of homoserine lactone levels as a means of controlling pathogenicity. Certain algae have been demonstrated to produce competitive inhibitors of acyl-homoserine lactones (AHL's) such as furanones (Masefield, 1999), as have some terrestrial plants. These compounds displace the AHL signal molecule from its receptor protein and can act as agonist or antagonist in AHL bioassays (Tepletski et al., 2000). Other methods employed to reduce HSL concentration include the development of auto-inducer inactivation enzymes (AiiA's) that catalyse the degradation of HSLs.

There are a number of potential problems and limitations associated with the therapies currently under development. It is as yet unproven as to whether vaccines will be efficacious treatments. Ps. aeruginosa produces an extensive mucoid capsule that effectively protects against opsonisation by host antibodies, as revealed by patients with persistent infections having high serum titres of anti-Pseudomonas antibodies. A limitation in the applicability of treatments such as vaccines and anti-PcrV antibodies, as described in U.S. Pat. No. 6,309, 651, is that these approaches restrict themselves to Pseudomonas infection, and would not be efficacious against other bacteria. The use of auto-inducer mimics are limited by the concentrations of most that are required to effectively compete against HSLs for the receptor binding site, and the possibility of side effects. It is well known that HSLs released by Pseudomonas and other bacteria have a number of direct effects on human physiology. These include inhibition of histamine release as described in WO 01/26650. WO 01/74801 describes that HSLs are also able to inhibit lymphocyte proliferation and down-regulate the secretion of TNF-α by monocytes and macrophages, so acting as a general immuno-suppressant. There is a danger therefore that therapies involving the use of competitive HSL mimics may result in down-regulation of the patient's immune system. This would be generally undesirable, and particularly so in immuno-compromised patients. The use of antibiotics can, at best, be viewed as a short-term strategy in view of the remarkable ability of this bacterium (and others) to develop resistance to antibiotics.

That the pathogenesis of Ps. aeruginosa is clearly multifactoral is underlined by the large number of virulence factors and the broad spectrum of diseases associated with this bacterium. Many of the extra-cellular virulence factors required for tissue invasion and dissemination are controlled by cell-to-cell signalling systems involving homoserine lactone-based signal molecules and specific transcriptional activator proteins. These regulatory systems allow Ps. aeruginosa to adapt to a virulent form in a co-ordinated cell density dependent manner, and to overcome host defence mechanisms. Interference with such cell signalling and the associated production of virulence factors is a promising therapeutic approach to reducing illness and death caused by Ps. aeruginosa. The importance of such approaches is highlighted by the growing number of bacterial pathogens found to utilise similar cell-to-cell signalling systems.

In order to study the molecular basis of host-pathogen interactions, it is desirable to have available a suitable model system (non-human) in which the stimuli and mechanisms relating to pathogenicity in humans can be replicated. In the case of many diseases the pathogen concerned is intrinsically associated with one, or a few closely related species or groups, e.g. HIV. Other organisms can cause disease in a wide range of host, crossing the species, genus, and even kingdom barriers. Ps. aeruginosa is one such pathogen, being able to infect a variety of both plant, insect and animal species.

In recent years it has been demonstrated that Ps. aeruginosa strains that are able to cause disease in humans and mice are also able to kill the nematode worm Caemohabtidis elegans (Tan et al., 1999a, Tan et al., 1999b, Tan et al., 2000). More importantly, the pathogenicity of Ps. aeruginosa to C. elegans is regulated by the same cell density-dependant quorum sensing systems that control pathogenesis in humans. The recent completion of the sequencing of the genomes of both Ps. aeruginosa and C. elegans make this relationship ideal for the study of bacterial disease mechanisms. The fact that 36% of C. elegans proteins also have homologues in humans (Darby et al., 1999), and the ease with which C. elegans can be grown in the laboratory, have lead to its widespread use as a model for pathogenisis and host defences in humans (Kurz and Ewbank, 2000).

A variety of different mechanisms by which Ps. aeruginosa mediates killing of C. elegans have been identified. Tan et al., 1999a; 1999b, and Mahajan-Miklos et al., 1999, describe the use of a clinical isolate (strain PA14) that also infects mice and plants. By varying the growth conditions of the bacteria, subsequent application to *C. elegans* can result in either fast killing (within hours) or slow killing (within 3 to 4 days. The fast killing mechanism is dependant only on the Rhl quorum sensing system. Moreover, the use of cell-free medium in which *Ps. aeruginosa* have been appropriately grown, or heat killed extracts are equally effective as death is effected by diffusible pyocyanin toxin. In contrast the slow killing mechanism is reliant on both Las and Rhl systems and results in significant infection of the nematode gut. As death is probably a result of infiltration of the host by the bacteria, this assay provides the most useful nematode model for infection in animals. A third killing mechanism has been described by Darby et al., (1999). Here the use of *Ps. aeruginosa* strain PA01 (a known human pathogen) grown in brain-heart infusion medium results in rapid paralysis and death of *C. elegans*. As with the slow killing described earlier, paralysis is both Las and Rhl system-dependant.

There is a need to develop effective means of modulating the concentrations of HSLs and other bacterial cell signalling molecules involved in pathogenicity by methods that do not have adverse side effects, and are unlikely to be evaded by pathogenic bacteria in the foreseeable future.

SUMMARY OF THE INVENTION

The present invention provides for methods for controlling the virulence of human, animal and plant pathogenic bacteria by regulating the extra-cellular concentrations of bacterial cell signalling molecules. Whereas other treatments are restricted to a particular pathogen or group of pathogens, or to specific aspects of bacterial virulence, the present invention addresses bacterial virulence in general.

According to a first aspect of the present invention, there is provided an antibody to a lactone or lactone-derived signal molecule secreted by bacteria.

Antibodies according to the present invention can be polyclonal antibodies or monoclonal antibodies. Polyclonal antibodies can be raised by stimulating their production in a suitable animal host (e.g. a mouse, rat, guinea pig, rabbit, sheep, chicken, goat or monkey) when the antigen is injected into the animal. If necessary an adjuvant may be administered together with the antigen. The antibodies can then be purified by virtue of their binding to antigen or as described further below. Monoclonal antibodies can be produced from hybridomas. These can be formed by fusing myeloma cells and B-lymphocyte cells which produce the desired antibody in order to form an immortal cell line. This is the well known Kohler & Milstein technique (*Nature* 256 52-55 (1975)).

Techniques for producing monoclonal and polyclonal antibodies which bind to a particular protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to antigen. Thus the present invention includes antibody fragments and synthetic constructs. Examples of antibody fragments and synthetic constructs are given by Dougall et al in *Tibtech* 12 372-379 (September 1994). Antibody fragments include, for example, Fab, F(ab')$_2$ and Fv fragments (see Roitt et al [supra]). Fv fragments can be modified to produce a synthetic construct known as a single chain Fv (scFv) molecule. This includes a peptide linker covalently joining $V_H$ and $V_L$ regions which contribute to the stability of the molecule. The present invention therefore also extends to single chain antibodies or scAbs.

Other synthetic constructs include CDR peptides. These are synthetic peptides comprising antigen binding determinants. Peptide mimetics may also be used. These molecules are usually conformationally restricted organic rings which mimic the structure of a CDR loop and which include antigen-interactive side chains. Synthetic constructs also include chimaeric molecules. Thus, for example, humanised (or primatised) antibodies or derivatives thereof are within the scope of the present invention. An example of a humanised antibody is an antibody having human framework regions, but rodent hypervariable regions. Synthetic constructs also include molecules comprising a covalently linked moiety which provides the molecule with some desirable property in addition to antigen binding. For example the moiety may be a label (e.g. a detectable label, such as a fluorescent or radioactive label) or a pharmaceutically active agent.

In order to generate anti-bacterial signal molecule antibodies, it is preferable to conjugate the target molecule, or a suitable derivative, to two different carrier molecules (proteins), though a single conjugated species can be also used. Bacterial signal molecules, in general, are too small to stimulate an immune response in-vivo, or to be used directly as a source of antigen for the selection of high affinity antibodies from antibody libraries. Selection of antibodies specific for the cell signalling molecule (hereafter referred to as 'antigen') is carried out in the preferred embodiment using a repertoire (library) of first members of specific binding pairs (sbp), for example a library of antibodies displayed on the surface of filamentous bacteriophage. Any other system that allows for the selection of specific receptors from a library of receptors is also applicable for the methods of the present invention. In alternative embodiments signal molecule-specific clones can be selected from a panel of antibody secreting hybridoma cell lines generated from an animal immunised with an antigen conjugate. For the purposes of a general illustration the example of a library of antibody binding sites displayed on phage particles will be used.

A conjugate comprising an antigen coupled to a suitable carrier molecule, which can be a protein, a peptide or any natural or synthetic compound or material (referred to hereafter as 'conjugate-1') is immobilised onto a suitable solid support such as an 'immunotube' or microliter plate, and the uncoated surface blocked with a non-specific blocking agent such as dried milk powder. Suitable conjugate molecules can include, but are not limited to proteins such as bovine serum albumin (BSA), Keyhole Limpet Haemocyanin (KLH), Bovine Thyroglobulin (TG), Ovalbumin (Ova), or non-proteins such as biotin. The only restriction on the selection of the conjugate molecule is that it be immobilisable in some way and for immunisation is large enough to elicit an immune response.

A library of first members of specific binding pairs (sbp's) ('the library') is applied to the immobilised conjugate and incubated for sufficient time for sbp members recognising conjugate-1 to bind. Phage not recognising the conjugate are removed by stringent washing. Phage that remain bound are eluted, for example with tri-ethylamine or other suitable reagent, into a buffer solution to restore neutral pH. Recovered phage particles are then infected into a suitable host organism, e.g. *E. coli* bacteria, and cultured to amplify numbers of each selected member and so generate a second 'enriched' library. The process is then repeated using the enriched library to select for phage-antibodies ('phage') recognising the antigen conjugated to a second carrier protein (conjugate-2), Additional rounds are performed as required, the selection process being altered to favour selection of those sbp members recognising the free form of the antigen. Phage are selected against antigen conjugates as described previously, using initially conjugate-1, and alternating with conjugate-2 (where available) for each subsequent round. Bound phage are elated by incubating with a solution of free antigen, or antigen conjugated to small soluble selectable moieties, e.g. biotin, for sufficient time for sbp members with higher affinity for the bound form of the antigen to dissociate from the immobilised conjugate. Those phage eluted with free antigen are infected into *E. coli* cells for amplification and re-selection, and those remaining bound to the immobilised antigen discarded. Alternatively, but less preferably, all antibodies binding to conjugate may be eluted eg. with low pH.

Individual (monoclonal) phage clones from each round of selection are screened for desired binding characteristics. This can be performed by a variety of methods that will be familiar to those with ordinary skill in the art, depending on requirements, including such techniques as SPR (Surface Plasmon Resonance) and ELISA (Enzyme Linked Immuno-Sorbant Assay). Selection criteria will include the ability to bind preferentially to the free soluble form of the antigen in the presence of conjugated derivatives.

In the preferred embodiment of the invention, antibodies will be generated from a naïve human antibody phage display library (McCafferty et al., Nature 348: 552-554, 1990; and as described in WO 92/01047). Thus the antibodies could be used for administering to patients in addition to use as diagnostic or dialysis reagents. In a diagnostic assay the antibody could be used to determine the presence and concentration of HSLs in patients and so predict the patient's infection status. In other embodiments a library can be constructed from an animal pre-immunised with one or more conjugates of a HSL and a suitable carrier molecule. A further alternative is the generation of hybridoma cell lines from an animal immunised as described above. In the latter two cases it is preferable that steps be taken to reduce the immunogenicity of resulting antibodies, for example by creating host animal-human chimaeric antibodies, or "humanisation" by CDR grafting onto a suitable antibody framework scaffold. Other methods applicable will include the identification of potential T-cell epitopes within the antibody, and the subsequent removal of these e.g. by site-directed mutagenesis (de-immunisation). In a further embodiment the antibody can be engineered to include constant regions from different classes of human immunoglobulin (IgG, IgA, etc.) and produced as a whole antibody molecule in animal cells. In particular these approaches are desirable where the antibodies are to be used therapeutically For the present invention, the antibody may be monoclonal or polyclonal. The antibodies may be human or humanised, or for dialysis/diagnostic applications may be from other species. Antibody fragments or derivatives, such as Fab, F(ab') .sup.2 (also written as F(ab')$_2$), Fv, or scFv, may be used, as may single-chain antibodies (scAb) such as described by Huston et al. (Int. Rev. Immunol. 10: 195-217, 1993), domain antibodies (dAbs), for example a single domain antibody, or antibody-like single domain antigen-binding receptors. In addition to antibodies, antibody fragments and immunoglobulin-like molecules, peptidomimetics or non-peptide mimetics can be designed to mimic the binding activity of antibodies in preventing or modulating bacterial infection by inhibiting the binding of cell-signalling molecules.

After the preparation of a suitable antibody, it may be isolated or purified by one of several techniques commonly available (for example, as described in *Antibodies: A Laboratory Manual*, Harlow and Lane, eds. Cold Spring Harbor Laboratory Press (1988)). Generally suitable techniques include peptide or protein affinity columns, HPLC or RP-HPLC, purification on Protein A or Protein G columns, or combinations of these techniques. Recombinant antibodies can be prepared according to standard methods, and assayed for specificity using procedures generally available, including ELISA, ABC, dot-blot assays etc.

The lactone signal molecule may be a homoserine molecule, or a peptide thiolactone molecule.

The homoserine lactone molecule can have a general formula selected from the group consisting of:

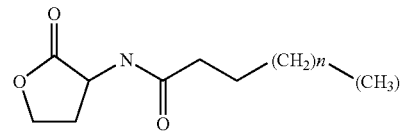

Formula I

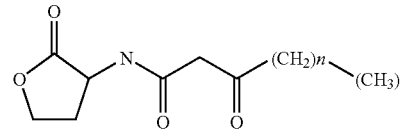

Formula II

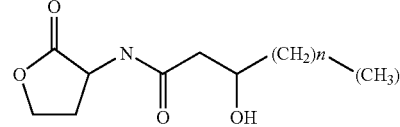

Formula III where n=0 to 12.

Compounds of general formula I can be described as acyl-homoserine lactone molecules. Compounds of general formula II can be described as 3-oxo-homoserine lactones. Compounds of general formula III can be described as 3-hydroxy-homoserine lactones.

Preferred homoserine lactone molecules for general formula I are N-butanoly-L-homoserine lactone (BBL) where n=0, N-dodecanoyl-L-homoserine lactone (dDHL) where n=8 and n-tetradecanoyl-L-homoserine lactone (tDHL) where n=10. Preferred homoserine lactone molecules for general formula II are N-(-3-oxohexanoyl)-L-homoserine lactone (OHHL) where n=2 and N-(-3-oxododecanoyl)-L-homoserine lactone (OdDHL) where n=8. Preferred homoserine lactone molecules for general formula III are N-(-3-hydroxybutanoyl)-L-homoserine lactone (HBHL) where n=0.

In general the bacterial HSLs can be further subdivided into two classes: i) long chain molecules (10-12 carbons) and ii) short chain molecules (4-8 carbons). In *Pseudomonas* sp these different size classes bind to different R molecules and cause different genes to be switched on. Long chain molecules bind to the R homologue gene product known as LAS and short chain molecules to the RHL protein homologue.

The peptide thiolactone can have a general formula (IV) as follows:

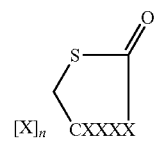

where X is any amino acid and n=1 to 10.

In the above, and throughout this specification, the amino acid residues are designated by the usual IUPAC single letter nomenclature. The single letter designations may be correlated with the classical three letter designations of amino acid residues as follows:

A=Ala G=Gly M=Met S=Ser
C=Cys H=His N=Asn T=Thr
D=Asp I=Ile P=Pro V=Val
E=Glu K=Lys Q=Gln W=Trp
F=Phe L=Leu R=Arg Y=Tyr

Preferred peptide thiolactone molecules may have the following structures:

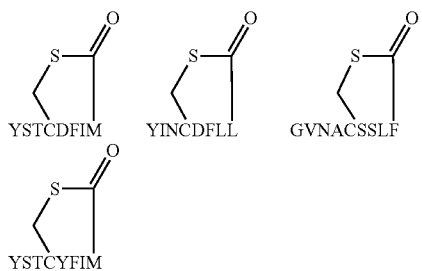

A growing number of bacterial species are being found to communicate between cells using a variety of small signal molecules. Gram-negative bacteria predominantly use N-acyl homoserine lactones (Table 1). The latter are a group of compounds that share a common homoserine lactone ring structure and vary in the length and structure of a side chain (FIG. 1a). There are three classes within the group, the acyl-homoserine lactones, the 3-oxo-homoserine lactones and the 3-hydroxy-homoserine lactones. A single species can produce and respond to members of more than one class.

The lactone-derived signal molecule may be a furanosyl borate diester, for example, AutoInducer-2 or AI-2, Pro-AI-2 or a Pro-AI-2-reactive hapten (FIG. 1b). Many gram negative and gram positive organisms such as *Vibrio harveyi* and *Bacillus anthracis* produce a second signal molecule, AI-2, that is derived from the same S-Adenosylmethionine source as homoserine lactones, and binds to the receptor LuxP (FIG. 1b). It is thought likely that AI-2 is a universal bacterial signal molecule, being produced and recognised by and induces virulence in a wide variety of species.

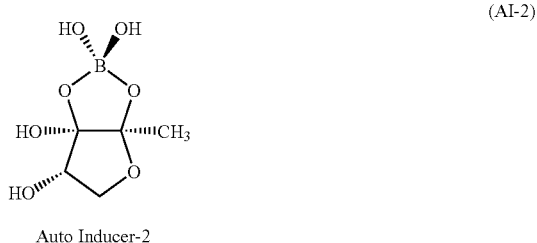

Auto Inducer-2

AI-2 can be described as 2,3-dihydroxy-4-methyl-3,4-borate diester.

A lactone-derived signal molecule can also be a derivative of 4,5-dihydroxy-2,3-pentanedione (DPD) which cyclizes naturally to form Pro-AI-2, which reacts naturally with boric acid to form AI-2 (FIG. 1b). Pro-AI-2 can be described as 2,4-dihydroxy-4-methyl-furan-3-one. Pro-AI-2 can be derivatised as shown in FIG. 1b at the 4-methyl position to add a heptanoic acid moeity to form a Pro-AI-2 reactive hapten. Other derivatives may also include other straight chain or branched, saturated or unsaturated $C_1$-$C_{10}$ carboxylic acid moieties, such as methanoic, ethanoic, propanoic, pentanoic, hexanoic, heptanoic, octanoic, nonanoic or decanoic acid.

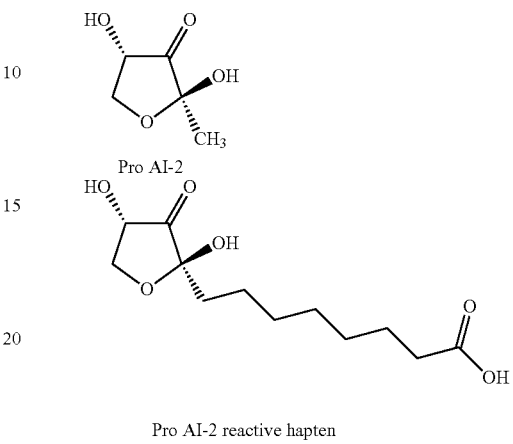

Pro AI-2

Pro AI-2 reactive hapten

Gram-positive bacteria such as *Staphylococcus aureus* use short peptides (FIG. 1c) (Mayville et al., 1999). The cells use the molecules as a means of determining the local cell density, such that in conditions of low cell density the concentration of signal molecule is correspondingly low. In high cell densities the local signal molecule concentration is high. When this concentration reaches a threshold level it induces the transcription of genes involved in virulence and the onset of a disease state in the host.

The thiolactone derivatised peptide signal molecules used by *Staphylococcus* spp. have additional biological functions. They not only provide the bacteria with information about their local population density, but they also serve to suppress virulence in other *S. aureus* belonging to different sub-groups (Lyon et. al., 2000). This bi-functionality is split between the different structural elements of the peptide, with the thiolactone C-terminus inhibiting virulence in other sub-groups. The un-modified N-terminus acts as the signal to up-regulate virulence gene expression in the sub-group that synthesised it, but only in conjunction with the C-terminus, which is also required. The presence of a truncated peptide comprising the C-terminal 5 amino acids with thiolactone linkage suppresses not only the other three sub-groups, but also the strain that produced it. Thus it follows that an antibody that recognises the N-terminus of the signal peptide, and effectively displays the C-terminus by leaving it exposed, will effectively suppress virulence in all *S. aureus* strains. Antibodies of the present invention may therefore be raised against an epitope presented by the thiolactone molecule as described above or a structural element thereof, for example the peptide sequence or the thiolactone moiety.

In certain preferred embodiments of the invention, the antibodies are scAbs, in particular scAbs that are obtained from *E. coli* clones designated as XL1-Blue G3H5, G3B12, G3G2 and/or G3H3. The clones have been deposited at NCIMB, Aberdeen, UK on 18 Mar. 2003 under the terms of The Budapest Treaty under the following accession numbers: G3H5 deposited as NCIMB-41167, G3B12 deposited as NCIMB-41168, G3G2 deposited as NCIMB-41169 and G3H3 deposited as NCIMB-41170. The strains may be cultivated in an appropriate growth media such as LB media supplemented with 100 µg/ml ampicillin, optionally supplemented with 12.5 µg/ml tetracycline, and/or 1% glucose, under standard conditions of 37° C. in air.

Bacterial signalling molecules are being discovered in every organism for which they are searched. It seems to be a ubiquitous system, applicable to every species. The main differences are that all gram negative (gram −ve) bacteria use homoserine lactone-based molecules, and gram positive (gram +ve) bacteria use (modified) small peptides. Many gram negative and gram positive organisms such as *Vibrio harveyi* and *Bascillus anthracis* (Jones, M. B. and Blaser, M. J.) also use a small boron-containing organic molecule AI-2 (AutoInducer-2) which, like homoserine lactones, is derived from S-Adenosylmethionine. Previous work in this field has concentrated on mimicking signal molecules with ones that are recognised but that do not function, i.e. no pathogenic switching, or on blocking the various receptor systems. The disadvantages of these methods are principally that resistance can be developed to the mimic or block and the 'real' signal molecule is still there and will compete for binding. In addition, some bacterial signalling molecules e.g. homoserine lactones are virulence factors in their own right, and can directly cause immuno-suppression of the host (i.e. patient). The essence of the present invention is to target the actual signal molecule, and this can be applied to all bacterial cell-to-cell signalling systems (gram negative and gram positive). This approach has a key and important advantage over all previous efforts in the field in that the bacteria will not recognise that they are being attacked, they will simply detect that that they are alone. There will not be any selective pressure for resistance.

According to a second aspect of the present invention, there is provided a pharmaceutical composition comprising an antibody as defined in the first aspect of the invention.

Such compositions may be prepared by any method known in the art of pharmacy, for example by admixing the active ingredient with a carrier(s), diluent (s) or excipient(s) under sterile conditions.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carriers) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions)

Suitable excipients for tablets or hard gelatine capsules include lactose, maize starch or derivatives thereof, stearic acid or salts thereof.

Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3 (6), page 318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the pharmaceutical compositions of the present invention can vary between wide limits, depending upon the disease or disorder to be treated, the age and condition of the individual to be treated, etc. and a physician will ultimately determine appropriate dosages to be used.

Such compositions may be formulated for human or for veterinary medicine. The present application should be interpreted as applying equally to humans as well as to animals, unless the context clearly implies otherwise.

According to a third aspect of the invention, there is provided a method for the treatment of bacterial infection of a subject, the method comprising administration of an antibody of the first aspect of the invention to the subject.

Examples of bacteria found to cause disease states are shown in Table 1. Methods of this aspect of the invention therefore extend to a method of treatment of an infection by a strain of bacteria as shown in Table 1 in a subject. In a preferred embodiment of the invention, there is provided a method of treatment of an infection of *Pseudomonas aeruginosa* in a subject.

Therapeutic substances of the present invention may be used in the treatment of a human or non-human animal. The treatment may be prophylactic or may be in respect of an existing condition.

The antibody will usually be supplied as part of a sterile, pharmaceutical composition which will normally include a pharmaceutically acceptable carrier. This pharmaceutical composition may be in any suitable form, (depending upon the desired method of administering it to a patient).

It may be provided in unit dosage form, will generally be provided in a sealed container and may be provided as part of a kit. Such a kit of parts would normally (although not necessarily) include instructions for use. It may include a plurality of said unit dosage forms.

The methods of the invention can be applied to short or long-term, acute or chronic illness/disease, and is effective against most or all bacterial pathogens of plants, animals, including humans. The invention can also be used as a prophylactic treatment for the prevention of disease onset in individuals at risk of or from exposure to pathogenic bacteria. The invention also has the potential to limit or prevent the down-regulation of the immune system that results from many infections, and is of particular concern with patients suffering from cancer, cystic fibrosis, AIDS and other immuno-suppressive conditions. Furthermore, as the methods of the invention are directed particularly at bacterial cell signalling molecules, and not primarily at the bacterial cells themselves, there will be no selective pressure exerted on bacterial populations to develop resistance to the treatments described.

The antibody may be administered to infected patients in order to modulate and reduce bacterial infection. This can include inhalation of the antibody in an aerosol by cystic fibrosis patients to increase life expectancy.

In yet another embodiment the antibody is administered to immuno-suppressed patients in order to increase immuno-competence.

In yet another embodiment conjugates of cell signalling molecules to immunogenic proteins can be administered to individuals or patients in order to stimulate an immune response against the signalling molecule resulting in the generation of neutralising antibodies.

In yet another embodiment the antibody is used as an immuno-diagnostic reagent to detect the presence of, and/or pathogenic status of potential pathogens, for example in the bloodstream or pleural fluids of patients.

In yet another embodiment the antibody is used as an immuno-capture reagent to selectively remove bacterial cell signalling molecules from patient's blood in a form of dialysis.

In yet another embodiment alternative methods can be applied to the removal of bacterial cell-cell signalling molecules from the blood of a patient with a view to modulating the pathogenicity and virulence of infecting micro-organisms. This can be achieved with other natural receptors or molecules based on natural receptors that bind to said signal molecules. Alternatively non-natural receptors can be applied such as molecularly imprinted polymers (MIPs). This class of receptor have already been shown to be able to bind specifically to small molecular weight bio-molecules such as drugs (Hart et al., 2000) and steroids (Whitcombe et al., 1995; Ramstrom et al., 1996; Rachkov et al., 2000). In a further alternative dialysis can be achieved by the non-specific removal of all small molecular weight molecules from the patient's blood as is kidney dialysis.

In yet another embodiment the receptor may have catalytic or enzymatic activity, and be able to convert the cell signalling molecule into a form that is no longer recognised by the target organism, or no longer results in pathogenic switching.

In yet another embodiment the antibody is used in one or more of the above applications in combination, or in combination with other therapies, for example antibiotics, to provide additive and enhanced therapeutic regimes, disease monitoring and treatment management.

The antibodies (or equivalent) of the present invention could be administered to treat bacterial infection, or used as a preventative measure for those at high risk of infection. In the case where infection already exists, the antibodies may be administered alone or in combination with anti-bacterial antibodies or antibiotics or other anti-microbial treatments. Administration of anti-HSL antibodies in conjunction with other therapies may allow the use of shorter courses or lower doses of therapeutics, so decreasing the risk of resistance arising and improving patient compliance.

According to a fourth aspect of the invention there is provided an antibody as defined in the first aspect for use in medicine.

According to a fifth aspect of the invention, there is provided the use of an antibody as defined in the first aspect in the preparation of a medicament for the treatment of bacterial infection.

According to a sixth aspect of the invention, there is provided a method of screening a population of specific binding molecules for an anti-bacterial specific binding molecule, the method comprising conjugating a bacterial lactone signal molecule to a carrier molecule and using the conjugate so formed to identify a specific binding molecule that specifically binds to the conjugate from the population of specific binding molecules.

Such methods are therefore a means for identifying a specific binding molecule that can be used as an anti-bacterial agent, for example in the treatment of a bacterial infection. The specific binding molecule is an antibody or a fragment thereof, for example a monoclonal antibody, or a polyclonal antibody. Suitably the carrier molecule is a protein as described above. The population of specific binding molecules may be a phage display library.

Specific binding molecules identified by a method of the present invention may be used in medicine or a method of treatment as described above. The specific binding molecules may further be used in the preparation of a medicament for the treatment of a bacterial infection.

Such methods therefore extend to uses of a bacterial lactone signal molecule to screen a population of specific binding molecules in order to identify a specific binding molecule that specifically binds to said bacterial lactone signal molecule.

According to a seventh aspect of the invention, there is provided a method of treatment of a bacterial infection of a subject, the method comprising isolation of a bacterial lactone signal molecule in a sample from said subject and using said bacterial lactone signal molecule to screen a population of specific binding molecules for an anti-bacterial specific binding molecule to identify a specific binding molecule that specifically binds to the signal molecule, and administering said specific binding molecule so identified to a patient in need thereof.

Such methods permit the identification of specific binding molecules directed against the infecting bacterial organisms whose signalling molecules are found in the sample. The sample may be of blood, saliva, tissue, cerebro-spinal fluid, tears, semen, mine, faeces, pus, skin, or mucous secretions. Samples of blood may be of whole blood, or of fractionated blood, for example, blood plasma. Tissue samples may be a biopsy of any infected or potentially infected tissue or organ. Samples may also be taken from wounds or sites of injury or infection or potential infection. Samples of fluid from the lungs or the contents of the stomach or the intestines may also be used.

Preferred features for the second and subsequent aspects of the invention are as for the first aspect mutatis mutandis.

Other objects, features and advantages of the present invention, including but not limited to related applications in plant and animal hosts, will be apparent to those skilled in the art after review of the specification and claims of the invention.

It will be apparent to those of ordinary skill in the art that the compositions and methods disclosed herein may have application across a wide range of organisms in inhibiting, modulating, treating or diagnosing disease or conditions resulting from infection. The compositions and methods of the present invention are described with reference to Pseudomonas aeruginosa, but it is within the competence of one of ordinary skill in the art to apply the objects herein to other species.

The invention will now be further described by reference to the non-limiting example and figures detailed below.

DESCRIPTION OF FIGURES

FIG. 2 illustrates the genetic regulation of quorum or cell density dependent sensing. The cell signalling mechanism consists of two components: 1) the I gene (lasI and rhlI) homologues synthesise increasing quantities of bacterial cell signalling molecules (HSLs) throughout growth (hence quorum sensing), and 2) the concentration dependant binding of signalling molecules to a cognate R protein homologue (encoded by lasR and rhlR) which in turn can switch on a series of particular genes (operon), allowing bacteria to co-ordinate a density dependent phenotypic switch (eg. virulence, swarming).

FIG. 3 illustrates the principals of the bioluminescent reporter gene assay using plasmid pSB1075. A reduction in light output is indicative of the successful blocking of bacterial cell signalling.

FIG. 10 shows Table 1. Table 1 lists various bacterial phenotypes, with the cell signalling molecules and regulatory elements of the quorum sensing system that regulate them, for a range of organisms.

FIG. 11, comprising panels A-C, shows Tables 2, 3, and 4, respectively. FIG. 11a depicting Table 2 shows a summary of the sensitivities ($IC_{50}$) of anti-AHL scAbs to free antigen (dDHL-COOH) and to two AHL analogues (tDHL and OHHL) in competition with dDHL-BSA as determined by competitive inhibition ELISA. FIG. 11b depicting Table 3 shows a comparison of the kinetics of two anti-AHL scAbs binding to immobilised dDHL-BSA conjugate as determined by Surface Plasmon Resonance using a BIAcore 2000 instrument. The association constants (ka), dissociation constants (kd) and affinity constants (KA, KD) are given. FIG. 11c depicting Table 4 shows a summary of the sensitivities ($IC_{50}$) of anti-HSL clones derived from chain-shuffling to various HSLs. Enclosed in brackets ( ) below each new clone is the designation of the clone from which it was derived. The degree of increased sensitivity to antigen of new clones over the starting clone is given in brackets ( ) where applicable. Data compare the binding to fee HSLs in competition with dDHL-TG conjugate as determined by competition ELISA.

FIG. 12 shows Table 5. Table 5 shows the effects of anti-HSL scAbs in reducing the expression of the virulence factor elastase by *Ps. aeruginosa*. Data represent the ratio of clearance zone to colony area, expressed as a percentage compared to the PBS control (100%).

EXAMPLE 1

The examples described herein relate to Vibrio fisheri and *Pseudomonas aeruginosa*. These are given only as an example, the scope of the invention not being limited to the example but including all bacterial cell-to-cell signalling molecules that directly or indirectly regulate expression of genes involved in virulence or pathogenicity, and also including other signal molecule-induced phenotypic changes to bacterial cells such as but not limited to bioluminescence.

Figure 1A:
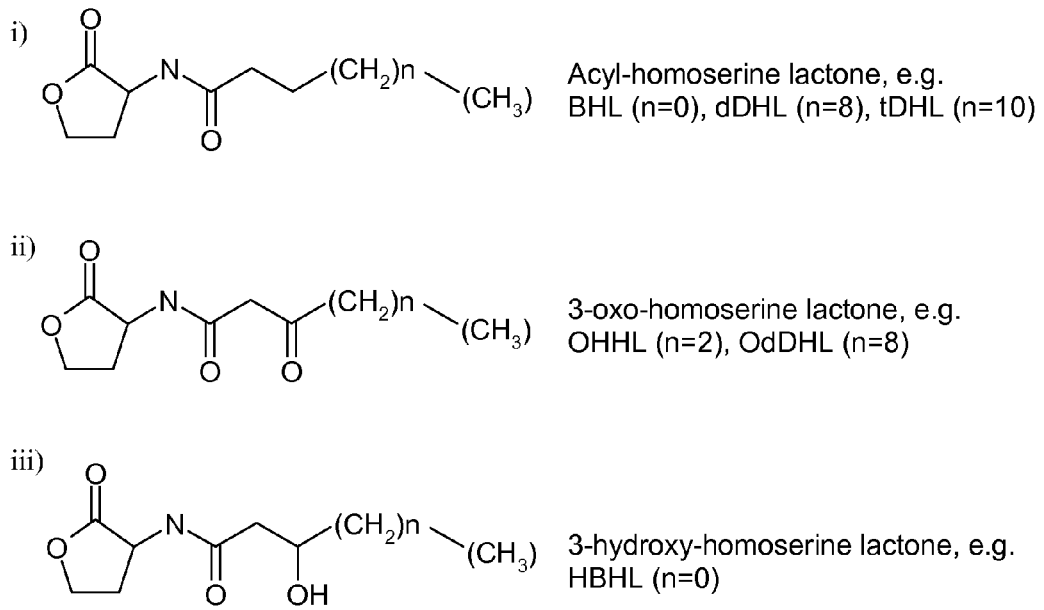
FIG. 1A shows the chemical structures of the three representative classes of homoserine lactone bacterial cell signalling molecules. These differ in the substitution at position C3, and vary within each class by the length of the acyl side-chain (typically n=0 to n=10). In addition, there may be a cis-bond present within the acyl chain.
Figure 1B:
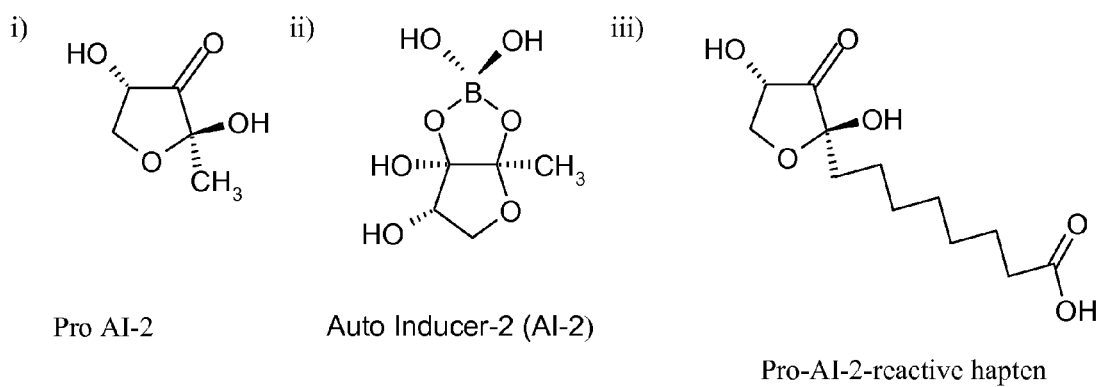
FIG. 1B shows the structures of i) pro AI-2, the immediate precursor of AI-2, ii) the boron-containing active AI-2 molecule and iii) the reactive pro-AI-2 hapten used to make conjugates.
Figure 1C:
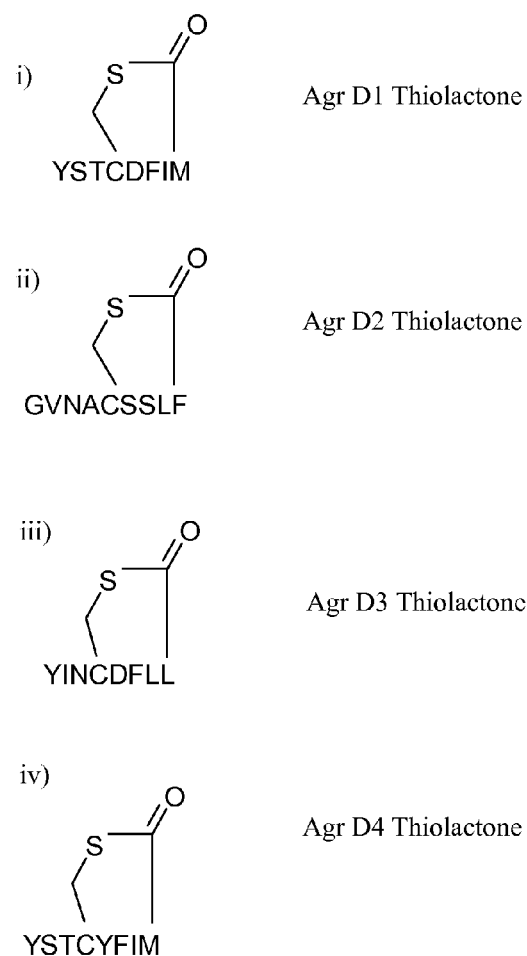
FIG. 1C shows examples of thiolactonc peptide signalling molecules used by i) Staphylococcus aureus Group I, ii) S. aureus Group II, iii) S. aureus Group III and iv) S. aureus Group IV.

A derivative of a HSL was synthesised (designated dDHL-COOH), having a twelve-carbon acyl chain acting as a 'linker', and terminating in a carboxylic acid group (see FIG. 1). This was conjugated, via the carboxylic acid group, to the carrier proteins Bovine Serum Albumin (BSA) and Keyhole Limpet Haemocyanin (KLH) to produce dDHL-BSA and dDHL-KLH. Briefly, 50 mg BSA or KLH was dissolved in 1.67 ml water, and to it added 3.3 ml of 2 mM $KH_2PO_4$ at pH 8.5, all at 4° C. To this, 1.05 ml dry dimethylformamide (DMF) was added drop-wise while stirring. Ten milligrams of activated N-hydroxysuccinimide ester of dDHL-COOH was dissolved in 100 µl dry DMF, and again added slowly to the carrier protein solution at 4° C. The reaction mixture was stirred well and allowed to stand for 24 h at 4° C. The conjugated material was then dialysed against 4×1 liter water, and conjugation confirmed by MALDITOF mass spectroscopy.

The term 'linker' refers to any chemical group used to allow attachment of the hapten (antigen) to a (preferably) immunogenic carrier molecule such that the hapten is displayed away from the surface of the carrier.

In alternative objects of the invention, other carrier molecules such as magnetic beads or biotin, and other linkers and conjugation strategies can be employed. The two conjugated forms of dDHL were then used to screen an antibody phage display library. Briefly, the library was screened for a total of 3 rounds of bio-panning. In each round a dDHL-conjugate was immobilised onto a solid support and incubated with the library of phage-antibodies for sufficient time for phage-antibodies recognising the conjugate to bind. Unbound phage were removed by stringent washing with PBS (Phosphate Buffered Saline) and PBS-Tween, and the remaining bound phage eluted by incubation at low pH (round 1). Eluted phage were then infected into *E. coli* bacteria and amplified by methods familiar to those practised in the art. The resulting amplified library of enriched clones was then used for the following round of panning. In order to reduce the numbers of clones selected that recognised the carrier protein, the immobilised conjugate (dDHL-BSA or dDHL-KLH) was alternated with successive rounds of selection. In order to bias selection in favour of clones recognising a specific HSL, the chosen HSL (dDHL-COOH) was used to competitively elute phage-antibodies during rounds 2 and 3, rather than low pH. Individual phage clones from round 3 were screened by ELISA: Each clone was assayed initially for the ability to bind to each of the dDHL-conjugates and to the carrier proteins alone. Those clones able to bind both conjugates but unable to bind either carrier protein were further assayed to identify those whose binding to conjugate could be inhibited by the presence of free dDHL-COOH in solution. The antibody variable region genes from those phage clones found to bind to free dDHL-COOH were sub-cloned into a soluble expression vector (pIMS 147), and produced as soluble single-chain antibody fragments (scAb) comprising the variable heavy and light chain domains joined by a flexible peptide linker, and a kappa constant domain from a human antibody. Quantification of the binding of soluble scAb to free HSLs was determined by competitive inhibition ELISA Samples containing a constant concentration of each selected scAb (with respect to 1 microgram per ml dDHL-BSA) were incubated with a range of concentrations of free dDHL-COOH (or dDHL-conjugate) for 1 h, then applied to an ELISA plate coated with dDHL-BSA. After 1 h incubation, unbound scAb was washed off and any scAb remaining bound to the immobilised conjugate detected with enzyme-labelled anti-human kappa antibody. The sensitivity of scAb for free dDHL-COOH, and cross reactivity with other HSLs (tDHL and OHHL) was determined from the concentration of free antigen that reduced the binding of scAb (without free antigen) to dDHL-BSA by 50% ($IC_{50}$) (Table 2).

The binding kinetics for anti-HSL scabs binding to dDHL-BSA was determined using a BIAcore 2000 (BIAcore, Sweden). A CM5 chip was activated with 0.2 M EDC [1-3-(3-dimethyl-aminopropyl)carbodiimide-HCl]/0.05 M NHS (N-hydroxy-succinimide), and dDHL-BSA or BSA alone coupled to the chip in 10 nM Na-acetate at pH 3.5 or 4.5 respectively. A series of 10 concentrations of scAb (100 to 1000 nM) were assayed in duplicate in HBS buffer at a flow rate of 20 microliters/min. Between samples the chip was regenerated with 20 microliters 100 mM NaOH. Kinetics were determined using the BIAevaluation 3 software package (Table 3).

The ability of the scAb G3B12 to bind to OHHL was further assessed by immobilising scAb to nickel-sepharose beads in a column via a 6×histidine tag, and passing a solution of OHHL through the column. Any OHHL bound by the scAb and retained on the column was subsequently eluted. The concentration of OHHL in the column flow though (i.e. unbound) and that bound and later eluted were determined.

The ability of the scAbs to bind to HSLs and to modulate the response of bacteria to AHLs was determined using *E. coli* strains JM107 containing the plasmid pSB401 (*Vibrio fischeri* response surrogate) and JM109 containing the plasmids pSB406 and pSB406 (*Pseudomonas aeruginosa* response surrogate). The reporter plasmids contain the HSL response regulator genes luxR (pSB401), lasR (pSB1075, responsive to long-chain HSLs) or rhlR (pSB406, responsive to short-chain HSLs), and the luxI promoter region, which together with exogenous HSLs activates expression of the luxCDABE gene fusion (the luminescence structural genes) from *Photorhabdus luminescens*. Under the appropriate growth conditions these cells are induced to emit light in response to the presence of extra-cellular HSLs, the intensity of light emitted being proportional to the concentration of HSL.

Soluble scAbs from clones selected from the library were expressed using published protocols (Strachan et al., 1998). During immobilised metal affinity chromatography purification (IMAC), scAb was not elated from the nickel-sepharose column. A series of additional scAbs with specificities to irrelevant antigens were also expressed and immobilised onto nickel-sepharose columns to act as controls. Five hundred microliters of 10 nM OHHL was applied to each column and incubated for 1 hour at 4° C. Columns were centrifuged at 40 g for 15 s and the flow through collected. Any bound OHHL was eluted with 250 microliters 1 M NaCl. The original flow through was re-applied and incubated as before, the flow through collected and bound HSL eluted with 1 M NaCl.

Figure 4:
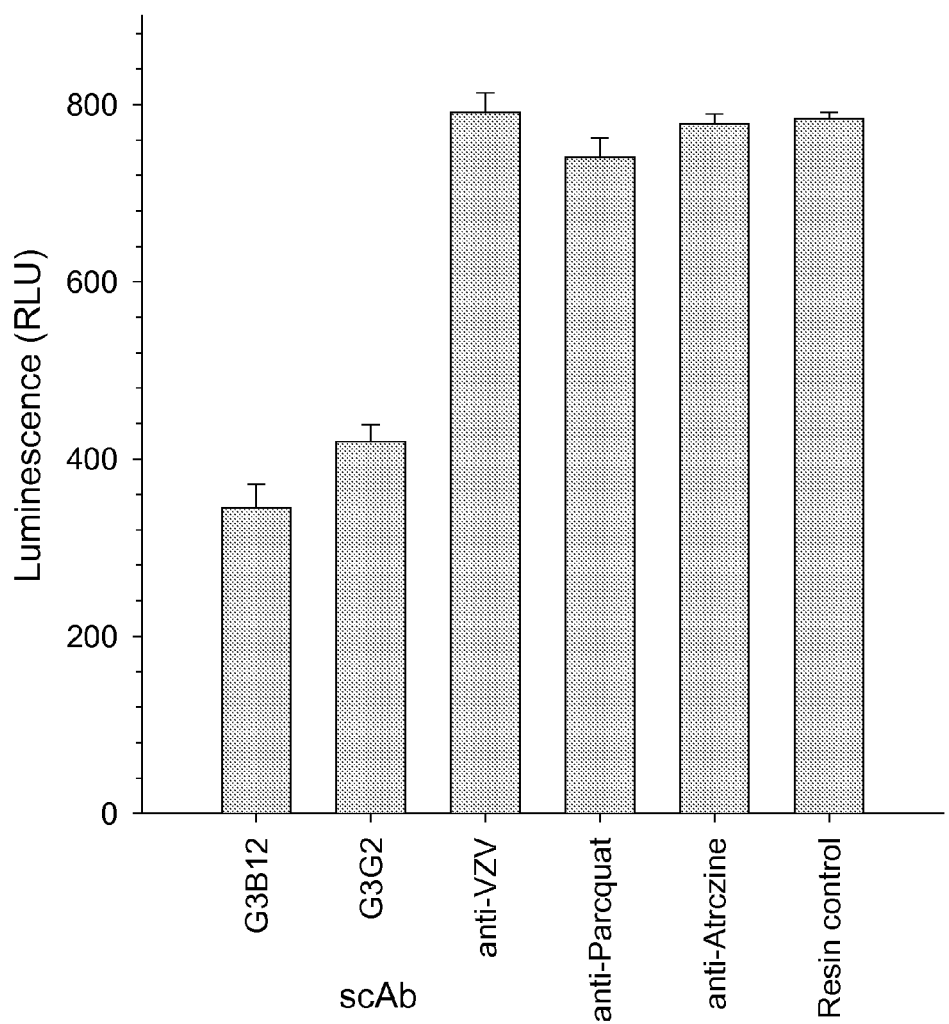
FIG. 4 shows a comparison of the abilities of HSL-specific and irrelevant single-chain antibodies immobilised onto an inert column matrix to remove HSL from solution by immuno-affinity capture. Column eluates were applied to an E. coli surrogate of Vibrio fischeri (JM107-pSB401) and the effect of residual HSL in the eluates determined from the subsequent stimulation of the bacterial cultures to fluoresce as measured by RLU. ScAbs G3B12 and 0302 are HSL-specific, anti-VZV is specific for a viral protein, anti-Paraquat and anti-Atrazine are specific for herbicides with molecular weights similar to HSL molecules, and the Resin control contained no immobilised scAb. Data represents the means of three replicate samples from two separate assays. Standard errors are indicated.

Samples of HSL solution prior to and after passage through the immobilised scAb column were applied to E. coli JM107 pSB401 cultures and the light emitted measured with a luminometer. Appropriate control experiments were carried out using a column to which no scAb had been immobilised, and three additional columns including scAb with specificity's for irrelevant antigens. Cells were grown shaking at 37° C. for 18 h in-LB medium containing tetracycline. One milliliter of the culture was inoculated into 100 ml LB tetracycline medium and grown at 37° C. until an OD 600 nm 0.2 was achieved. One hundred microliters of the culture was applied to replicate wells of a 96-well black bio-assay plate, and an equal volume of HSL solution added. HSL solutions were 10 nM OHHL (positive control), milli-Q water passed through a nickel-sepharose column (resin control), or the flow through from passing 10 nM OHHL over columns containing immobilised scAb as described above. Plates were incubated at 37° C. for 2 h with shaking, and luminescence read using an Anthos LUCY1 luminometer for 1 s (FIG. 4).

Figure 5:
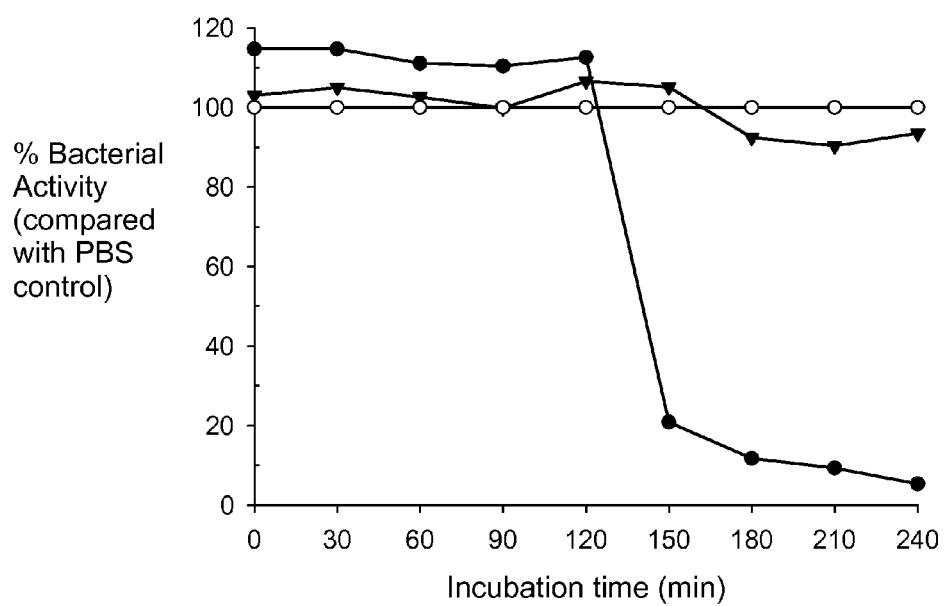
FIG. 5 shows the inhibitory effects of specific and irrelevant single-chain antibodies on the dDHL-mediated stimulation of an E. coli surrogate of Ps. aeruginosa (JM109-pSB1075) as measured by bioluminescence output. Data is given for the HSL-specific scAb 03115 (●), a non-specific control scAb (▼) (specific for a pathogenic bacterial surface protein), and in the absence of scAb (○). Data points represent the means of three replicate samples from replicate assays.
Figure 6:
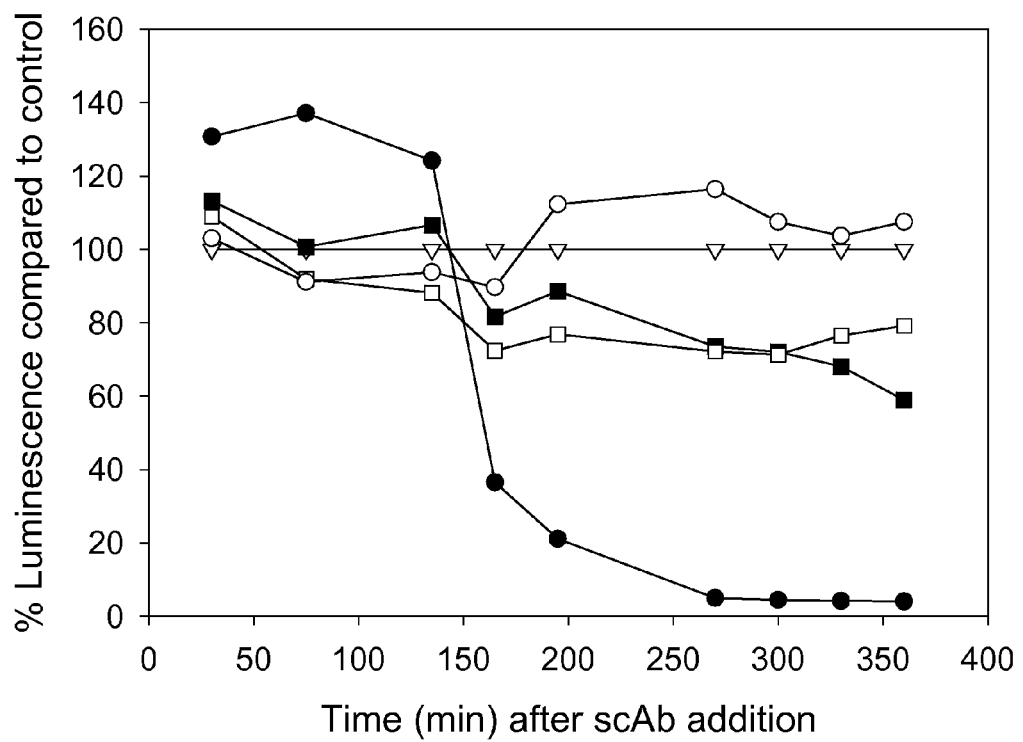
FIG. 6 shows the inhibitory effects of specific and irrelevant single-chain antibodies on the tDHL-mediated stimulation of an E. coil surrogate of Ps. aeruginosa (JM109-pSB1075) as measured by bioluminescence output. Data is given for three HSL-specific scAbs; G3H3 (●), G3G2 (■) and G3B12 (□), for the irrelevant anti-V scAb (○) (specific for a pathogenic bacterial surface protein), and in the absence of scAb (▽). Data points represent the means of three replicate samples from replicate assays.

The ability of the scAbs to reduce bacterial responses to long-chain HSLs was assessed with an HSL-inducible luminescence reporter bioassay over a period of 3.0 h using E. coli strain JM109-pSB1075. This strain is essentially as described for JM107-pSB401, the difference being that plasmid pSB1075 includes the lasR of Pseudomonas aeruginosa in place of the luxR of Vibrio fischeri. Single colonies of JM109-pSB1075 were inoculated into 10 ml LB broth with antibiotic and incubated overnight at 37° C. Two hundred microliters of overnight culture were inoculated into 10 ml fresh medium and incubated at 37° C. with shaking to OD 600 nm 0.2. HSL was added to the cultures (dDHL-COOH at 20 nM final conc'n or tDHL at 50 nM final conc'n) and one hundred microliters of culture was added to triplicate wells of a black 96 well plate. LB medium was added to negative controls. Either 50 microliters PBS or 50 microliters scAb at 2 mg/ml was added to each well and the plate incubated further for three hours shaking at 37° C., after which time luminescence was measured at 30 min intervals and the effect of scAb on cell signalling determined (FIGS. 5 and 6). The data demonstrates the ability of anti-HSL antibodies to cross react with structurally different homoserine lactone signal molecules, and to reduce or eliminate the response of a Ps. aeruginosa surrogate to extra-cellular HSL.

Figure 7A:
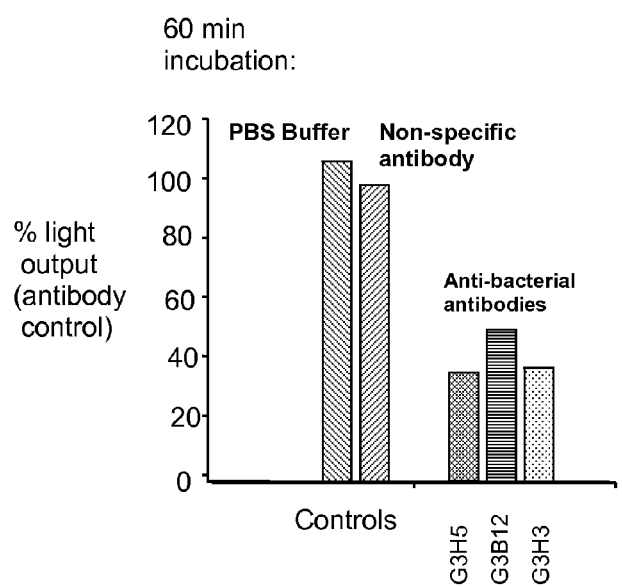
FIG. 7 shows the inhibitory effects of specific and irrelevant (non-specific) single-chain antibodies on the BBL-mediated stimulation of an E. coli surrogate (JM109-pSB406) of Ps. aeruginosa Rrhl system (short-chain HSL responsive) as measured by bioluminescence output after 60 min (FIG. 7A) and 150 min (FIG. 7B). Data is presented for G3H5, G3B 12 and G3H3 antibodies, a non-specific control antibody (specific for a pathogenic bacterial surface protein), and in the absence of antibody (PBS buffer only). Data points represent the means of three replicate samples from replicate assays.
Figure 7B:
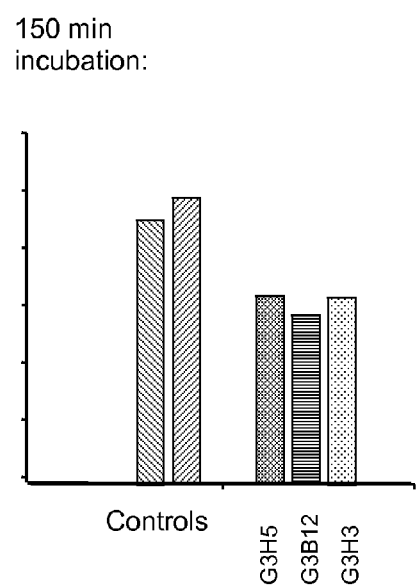

The ability of the scAbs to reduce bacterial responses to short-chain HSLs was assessed in a similar way to that described above. The bioluminescence reporter system used E. coli strain JM109 with the reporter plasmid pSB406, including the rhlR response element regulator. The signal molecule BHL (as acyl-HSL in FIG. 1 but 4 carbon side chain) was added to the E. coli cultures to 50 nM final concentration (an equivalent volume of LB medium was added to negative control cultures), and 100 µculture added to triplicate wells of the assay plate. Either 50 µl scAb at 100 nM or 50 µl PBS was then added, and plates incubated as described earlier. Measurements of luminescence were taken after 60 min and 150 min (FIG. 7).

EXAMPLE 2

To assess the ability of anti-HSL scabs to afford protection to animals against pathogenic Ps. aeruginosa, a 'slow-killing' assay using the nematode C. elegans was employed. This assay is based on the killing of the worms following establishment of a Ps. aeruginosa infection in the animal's gut.

Figure 8A:
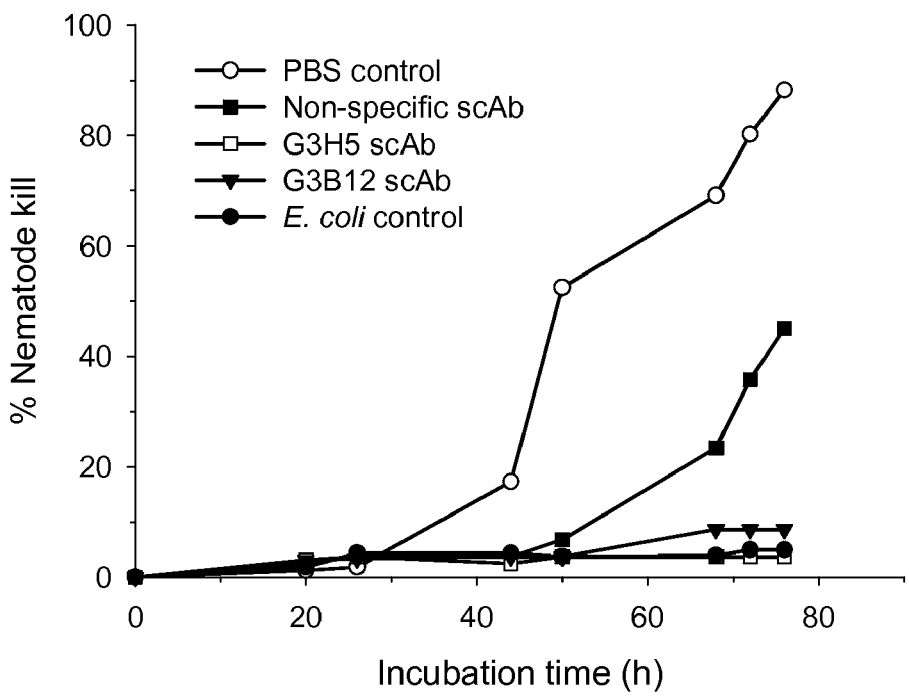
FIG. 8 shows the slow kill nematode assay demonstrating the ability of G3H5 and G3B 12 antibodies to protect nematodes against infection by the bacterial pathogen Pseudomonas aeruginosa strain PA14 (FIG. 8A) and Ps. aeruginosa strain PA01 (FIG. 8B).

Ps. aeruginosa strain PA14 was infected into 5 ml LB broth on day 1 and incubated overnight at 37° C. On day 2, 1% of the overnight culture was inoculated into 5 ml fresh LB with 100 µl scAb at 100 nM broth and incubated at 37° C. to OD 600 nm of 0.4. Ten microliters bacterial culture was spotted onto the centre of NG enriched peptone agar plates (nematode growth media), together with 50 µl scAb at 120 nM and plates incubated overnight at 37° C. On day 3 (pm) an additional 50 µl scAb (120 nM) was spotted onto the plates and incubation continued overnight. On day 4 (am) the plates were transferred to room temperature (~20° C.) and a further 50 µl scAb added. On day 5 (am), 50 µl scAb was added as before, and 20-5-adult worms added directly onto the bacterial lawn (time=0 h). Supplementary additions of scAb were made at time=26, 50 and 76 h. The numbers of dead worms were determined at intervals over the following 3 days (FIG. 8a). Worms were considered dead when non-motile and not responsive to touch by a fine wire pick.

For control plates either PBS or an irrelevant scAb (specific for an unrelated target antigen) were used, or worms were grown on E. coli strain OP50.

A second assay was also carried out using Ps. aeruginosa strain PA01 (Darby et al., 1999). This strain is used primarily for 'paralytic killing' (toxin production), but it also suitable, though less effective than PA14, for slow killing infection studies as in this example.

Figure 8B:
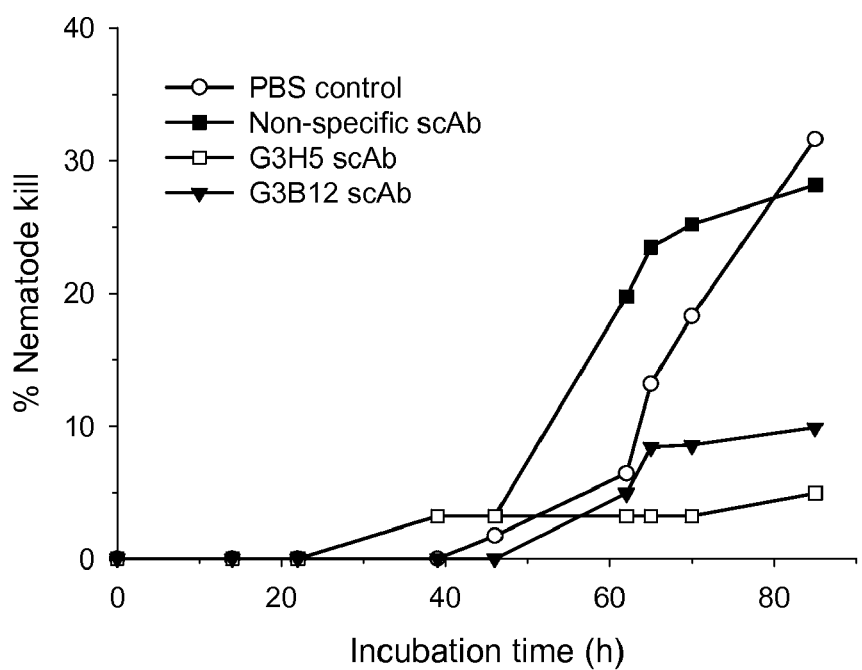

The assay was carried out as described above with the following modifications. Additions of scAb throughout were at 100 nM concentration. On day 3, 50 µl scAb was spotted onto plates in the morning and afternoon. After the second addition, the plates were transferred to room temperature and incubated overnight. Worms and scAb were applied on day 4 (time =0 h), and only two supplementary scAb additions made at t=30 and 60 h (FIG. 8b).

EXAMPLE 3

Ps. aeruginosa produces several extracellular products that, after colonisation, can cause extensive tissue damage. One of these, elastase, is essential for maximum virulence of Ps. aeruginosa during acute infection. The production of elastase is under the control of the lasI/R quorum-sensing cascade. The detection of elastase production can therefore be used as an indicator of the capacity for virulence of the bacterial population.

Four microliters Ps. aeruginosa strain PA14 at 10 sup 5 CFU per ml (low OD) or 10 sup 8 CFU per ml (high OD) were inoculated onto agar plates containing 1% elastin, 0.5% lab lemco powder, 1% peptone, 0.5% sodium chloride and 1.5% agar, and incubated at 37° C. for 5 days. Growth to low OD discourages pathogenic switching, whereas growth to high OD encourages pathogenic switching. Fifty microliters of scAb (200 nM) was added to the plates together with the bacteria, and additional applications of the same volume made at 24 h intervals throughout the assay.

The diameter of the bacterial colonies and the surrounding clear zones (indicative of lysis of elastin by elastase) were measured daily, and the elastolytic activity of the colonies determined as a ratio of the clear zone area to bacterial colony area. Again, 3-4 replicates per trial were performed and E. coli XL1-Blue was be used as a negative control (Table 5).

EXAMPLE 4

In order to isolate anti-HSL antibodies with higher affinity for antigen, and to direct specificity towards particular HSL variants, affinity maturation was performed on clone G3B12. Phagemid DNA was isolated from the G3B12 bacterial clone, and the variable light chain gene amplified by PCR using a 5' oligonucleotide primer, LINKER-REV comprising the last 30 bases of the 45 base-pair flexible linker region (5'-GGCG-GAGGTGGCTCTGGCCGGTAGTGC-3') and a 3' primer gIII-FOR (5'-GAATTTTCTGTATGAGG-3'), specific for the phage minor coat protein gene gIII. Product of the correct size (~380 bp) was electrophoresed in a 1% agarose gel, excised, and purified. In a similar way, phagemid DNA containing the entire human naïve library from which the original clone was isolated was prepared. The whole repertoire of variable heavy chain genes was amplified using the 5' primer AH1-REV (5'-AAATACCTATTGCCTACGGC-3') specific for the pelB leader sequence, and the 3' primer LINKER-FOR encoding the first 30 bases of the linker region (5'-AGAGCCACCTC-CGCCTGAACCGCCTCCACC-3'). Product of the correct size (~400 bp) was purified as above. The repertoire of VH genes was then combined with the monoclonal VL gene by linking PCR using the complementary 15 bases of the centre of the linker region that was common to both primary PCR products. The new library was amplified by addition of the primers AH1-REV and gIII-FOR to the linking PCR reaction after 4 cycles, and a further 25 cycles performed. The amplified DNA was digested with the restriction enzymes NcoI and NotI, and ligated into a similarly digested and purified phagemid vector. Ligated and re-purified DNA was finally transformed into E. coli strain TG1 cells by electroporation and plated in the conventional manner.

Phage antibodies were rescued with helper phage as before, and applied to immunotubes coated with dDHL-BSA conjugate, and allowed to bind. Unbound phage were poured off, and weak/non-specific binders removed by multiple wash steps with PBST and PBS. Conjugate specific phage were then eluted with low pH triethylamine and neutralised. These were infected into fresh log-phage TG1 cells, rescued, and amplified again for following rounds of selection (pans). For the successive pans, the immobilised conjugate was alternated between dDHL-BSA and dDHL-TG. During the third round of panning, the bound phage from the shuffled library were eluted from duplicate pans with either free dDHL or with BHL (butyrylhomoserine lactone).

After 3 rounds of panning, monoclonal phage-antibodies were screened for desired binding characteristics. Individual phage clones from round 3 were screened by ELISA: Each clone was assayed initially for the ability to bind to each of the dDHL-BSA and KLH conjugates and to the carrier proteins alone. Those clones able to bind both conjugates but unable to bind either carrier protein were further assayed to identify those whose binding to conjugate could be inhibited by the presence of free dDHL or HSL in solution. The antibody variable region genes from those phage clones found to bind to free BHL/dDHL were sub-cloned into a soluble expression vector (pIMS 147), and produced as soluble single-chain antibody fragments (scAb) comprising the variable heavy and light chain domains joined by a flexible peptide linker, and a kappa constant domain from a human antibody. Quantification of the binding of soluble scAb to free HSLs was determined by competitive inhibition ELISA. Samples containing a constant concentration of each selected scAb (with respect to 1 microgram per ml dDHL-TG) were incubated with a range of concentrations of free HSL for 1 h, then applied to an ELISA plate coated with tDHL-TG. After 1 h incubation, unbound scAb was washed off and any scAb remaining bound to the immobilised conjugate detected with enzyme-labelled anti-human kappa antibody. The sensitivity of scAb for free HSL, and cross reactivity with other HSLs was determined from the concentration of free antigen that reduced the binding of scAb (without free antigen) to dDHL-TG by 50% ($IC_{50}$) (Table 4).

EXAMPLE 5

Two conventional peptides, YST-1 (YSTGGAGSGG) and YST-2 YSTASGGASS were synthesised, together with a third version, YST-3, with biotinylation^ (^ denotes site of biotinylation) of the penultimate C-terminal lysine side chain (YSTAGGSGAK^S). A fourth thiolactone peptide YSTC*DFIM* (Agr-D1) was also synthesised, where * denotes residues connected by the thiolactone ring (see FIG. 1c). Some of YST-1 was conjugated to BSA and YST-2 to bovine thyroglobulin (TG) via the C-terminus using 1-ethyl-3-(3-dimethylaminopropyl) carbodiimide (EDC) by conventional conjugation chemistry.

A human naïve antibody library was panned for four rounds against alternating immobilised YST-1 and YST-2 conjugates essentially as described previously. After binding phage-antibodies for 1 h, unbound phage were poured away and weakly bound phage removed by extensive washing with PBST followed by PBS. Bound phage were eluted with thethylamine and neutralised, then infected into log phase E. coli TG1 cells. The enriched phage were amplified by rescuing with helper phage, then purified and concentrated by polyethylene glycol precipitation ready for the next round of selection. Following washing of phage bound to YST-1/2-conjugates in rounds 3 and 4, phage were eluted with a solution of YST-3. Those phage binding to the biotinylated peptide were captured by streptavidin coated paramagnetic beads and immobilised with a magnet. After further wash steps, the bound phage were added directly to TG1 Cells and allowed to infect as before.

Figure 9:
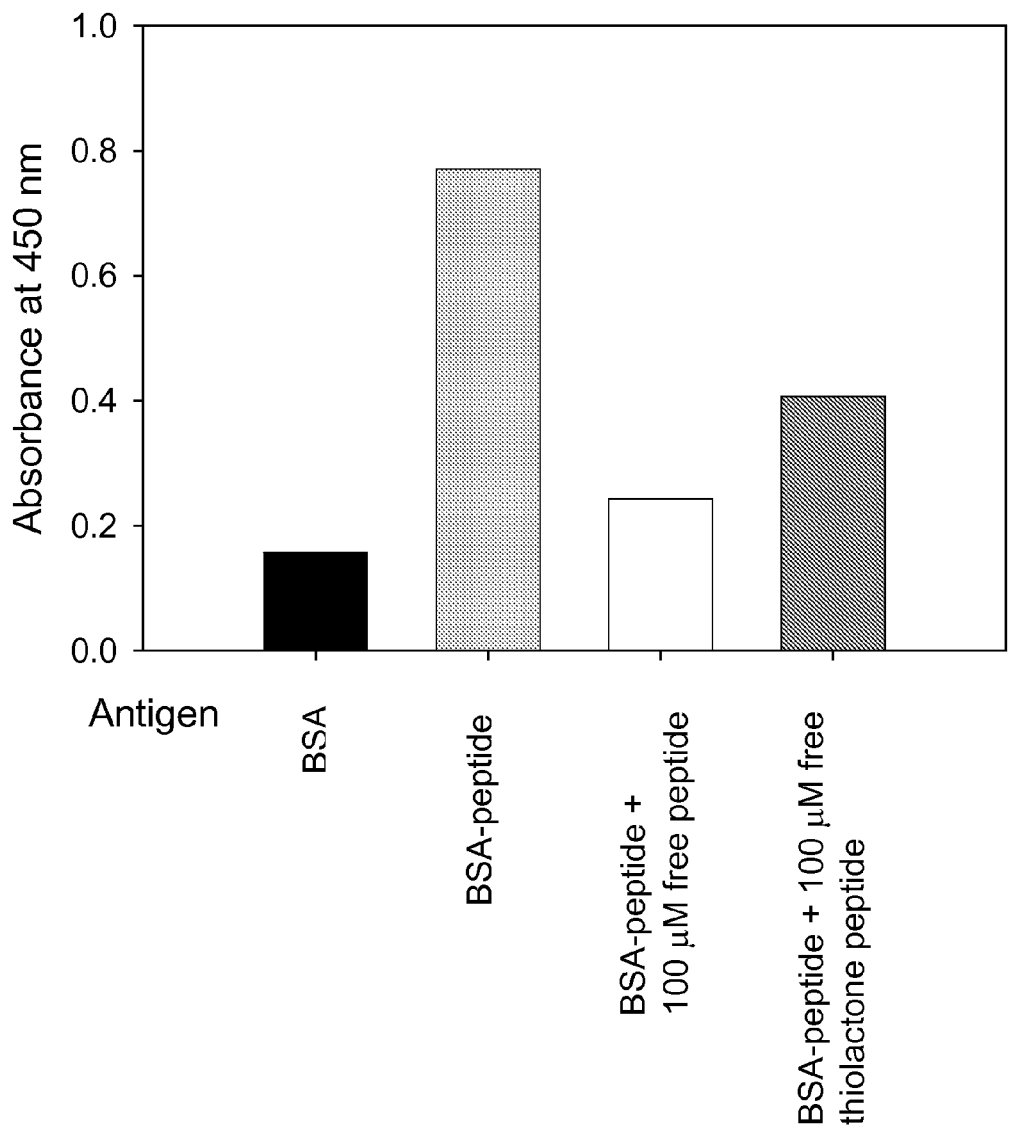
FIG. 9 shows competition ELISA data for anti-peptide scAb YST-1 binding to BSA control, or BSA-peptide conjugate in the presence or absence of free peptide 'YSTG-GAGSGG' or free thiolactone peptide Agr-D1 (see FIG. 1C).

Following four rounds of selection, monoclonal phage-antibodies were screened by ELISA for binding to YST-1 and YST-2 conjugates, and to BSA and TG carrier proteins alone. The scFv genes of those clones that bound only to both conjugates were sub-cloned into the pIMS-147 scAb soluble expression vector and transformed into E. coli XL1-Blue cells. These cells were expressed, and soluble scAb extracted from the bacterial periplasmic space and purified by Nickel affinity chromatography. Purified scAb was then further assayed for binding to free (non-conjugated) peptide and to the thiolactone-peptide autoinducer Agr-D1, in competition with immobilised peptide conjugates by ELISA. Signal reduction in the presence of peptide compared to binding to conjugate alone indicates that scAb is recognising the YST-epitope common to all peptides (FIG. 9).

EXAMPLE 6

In order to generate antibodies against the AI-2 target, both the free AI-2 molecule and a conjugated form are required. It is not (considered) possible to isolate AI-2 in a pure form. In nature, AI-2 is formed by the (spontaneous) reaction of pro-AI-2 (FIG. 1(b)) with boric acid. In vitro, pro-AI-2 will also react with boric acid to yield active AI-2, however this is not suitable for conjugation and antibody selection. A derivative of pro-AI-2 can be synthesised whereby the methyl group is replaced by a linker e.g. an acyl chain, with a terminal reactive group e.g. carboxylic acid. Any structure that includes a terminal reactive group suitable for chemical conjugation or cross-linking to a carrier, and that will result in the core pro-AI-2 moiety being displayed clear of the carrier surface, can be used as a linker. The reactive pro-AI-2 is conjugated to preferably two different carriers as described in the section 'summary of the invention'.

A library of potential receptors (e.g. an antibody library displayed on phage) is applied to an immobilised conjugate in the presence of boric acid (preferably >10 µM, pH 6.0-8.0) in order to yield immobilised AI-2 conjugate. Phage-antibodies ('phage') are allowed to bind, and those not recognising conjugate are removed by washing. Bound phage can be eluted with high or low pH e.g. triethylamine, or by competitive binding with free AI-2 or by competitive binding with e.g. biotinylated AI-2 followed by removal with magnetic streptavidin beads. During all stages of bio-panning except extreme pH elution, borate should be present to ensure that the correct structure of AI-2 is maintained. Eluted phage should be re-infected into host bacteria (*E. coil*), amplified by growing cells under phage-particle producing conditions and purified for the next round. Subsequent rounds of selection are carried out as described for round one except that, preferably, the immobilised conjugate is alternated.

When sufficient rounds selection have been completed, individual (monoclonal) clones can be assayed for binders to AI-2. It is probable that at least three rounds of selection will be needed, although AI-2 binding clones may be isolated after only one round, or it may be necessary to perform more than three rounds. Polyclonal phage-ELISA can be performed after each round by methods well known to those familiar with the art to determine how many rounds are required. Monoclonal phage-antibodies should be produced as described in earlier examples, and assayed for binding to each of the conjugates used for selection and to the respective un-conjugated carriers. Third or fourth conjugate(s) may be used additionally if available. Putative positive clones will be identified as those binding to all available conjugates in the presence of borate, but not to carrier molecules alone and preferably not to conjugate in the absence of borate.

As it is possible that the reaction of pro-AI-2 with borate may yield more than one species, it will be preferable to demonstrate that antibodies recognise in particular the correct AI-2 structure. This could be determined by assaying for binding to conjugate in the presence of free pro-AI-2 and borate. A reduction in binding with increasing concentrations of free pro-AI-2 is indicative of competitive inhibition. Such antibodies would therefore be expected to be able to modulate the response of AI-2 responsive bacteria by binding to extracellular AI-2 and rendering it unavailable to cells.

A suitable in vivo model can be found in bioluminescent *Vibrio harveyi*, a bacterium that bioluminesces in response to AI-2. Strains of *V. harveyi* that are LuxS⁻ are unable to synthesise DPD (a precursor of pro-AI-2), and so cannot produce AI-2. They are however able to respond by (increased light output) in response to exogenously added AI-2, either in the form of pro-AI-2 together with borate, or as borate-containing cell-free culture media obtained from LuxS⁺ *V. harvei*. The addition of borate alone to LuxS⁻ cells or to LuxP⁻ cells (lacking the natural AI-2 receptor) does not result in any light emission. Potential anti-AI-2 antibodies ('receptors') could therefore be identified as those fulfilling the binding criteria outlined earlier, and also being able to either deplete AI-2 from w.t. *V. harvei* culture media as determined by reduced light emission when added to LuxS⁻ cells, or to quench/prevent/reduce light emission when added to LuxS⁺ cells.

References Cited
U.S. Patent Documents

| 6,309,651 | October 2001 | Frank et al. |
|---|---|---|

Other Patent Documents

| WO 01/26650 | April 2001 | University of Nottingham |
| WO 01/74801 | October 2001 | University of Nottingham |
| WO 92/01047 | October 2001 | Bonnert et al. |

Other References
Williams et al., 1996 Microbiol-UK 142: 881-888
Stintzi et al., 1998 FEMS Microbial Lett. 166 (2): 341-345
Glessner et al., 1999 J. Bacterial. 181 (5): 1623-1629
Brint and, Ohman 1995 J. Bacterial. 177 (24): 7155-7163
Reimmann et al., 1997 Mol. Microbial. 24 (2): 309-319
Winzer et al., 2000 J. Bacteriol. 182 (22): 6401-6411
Gambello and Iglewski 1991 J. Bacterial. 173 (9): 3000-3009
Latifi et al., 1995 Mol. Microbiol 17 (2): 333-343
Passador et al., 1993 Science 260: 1127-1130
Pearson et al., 1994 Proc. Natl. Acad. Sci. USA. 91 (1): 197-201
Winson et al., 1995 Proc. Natl. Acad. Sci. USA. 92 (20): 9427-9431
Pesci et al., 1997 J. Bacteriol. 179 (10): 3127-3132
Toder et al., 1991 Mol. Microbial. 5 (8): 2003-2010
Gambello et al., 1993 Infect. Immun. 61 (4): 1180-1184
Ochsner et al., 1994 J. Bacteriol. 176, 2044-2054
Pearson et al., 1995 Proc. Natl. Acad. Sci. USA 92 (5) 1490-1494
Latifi et al., 1996 Mol. Microbiol 21 (6): 1137-1146
Winzer et al., 2000 J. Bacteriol. 182 (22): 6401-6411
Manefield et al., 1999 Microbiol. UK 145: 283-291
Tepletski et al., 2000 Mol. Plant Microbe. Interact., 13, 637-648
Tan et al., 1999a Proc. Natl. Acad. Sci. USA 96: 715-720
Tan et al., 1999b Proc. Natl. Acad. Sci USA 96: 2408-2413
Tan and Ausubel, 2000 Current Opinion in Microbiology 3: 29-34
Darby et al., 1999 Proc. Natl. Acad. Sci. USA 96: 15202-15207
Kurz and Ewbank, 2000 Trends Microbiol. Mar; 8 (3):142-144.
Mahajan-Miklos et al., 1999 Cell 96: 47-56
Jones, M. B. and Blaser, M. J. 2003 Infection and Immunity 71 (7): 3914-3919
Kohler and Milstein, 1975 Nature 256: 495-497
Roitt et al., 1989 Immunology $2^{nd}$ Edn, Churchill Livingstone, London
Dougall et al., 1994 TibTech 12: 372-379
McCafferty et al., 1990 Nature 348: 552-554
Huston et al., 1993 Int. Rev. Immunol., 10: 195-217
Mayville et al., 1999 Proc. Natl. Acad. Sci. USA 96: 1218-1223
Hart et al., 2000 J. Am. Chem. Soc., 122, 460-465
Whitcombe et al., 1995 J. Am. Chem. Soc., 117, 7105-7111
Ramstrom et al., 1996 Chem. & Biol., 3, 471-477
Rachkov et al., 2000 Anal. Chico Acta. 405, 23-29
Strachan et al., 1998 Biosens. Bioelectron. 13: 665-673

The invention claimed is:

1. A method of screening a naive human phage display library for an anti-bacterial monoclonal antibody, comprising:
   conjugating a bacterial lactone or lactone-derived signal molecule to a first carrier molecule to generate an enriched library; and
   screening said enriched library against the bacterial lactone or lactone-derived signal molecule conjugated to a second, different, carrier molecule to identify a monoclonal antibody that specifically binds to the free soluble form of the bacterial lactone or lactone-derived signal molecule from the enriched library in the presence of conjugated derivatives thereof.

2. A method as claimed in claim 1 in which the lactone signal molecule is a homoserine molecule or a peptide thiolactone molecule.

3. A method as claimed in claim 2 in which the homoserine lactone molecule has a general formula selected from the group consisting of:

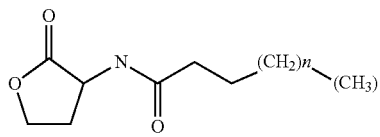
Formula I

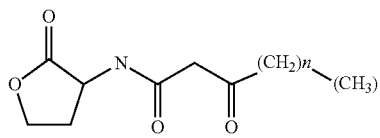
Formula II

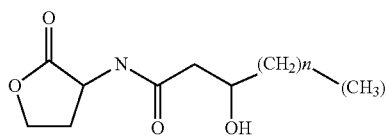
Formula III where n =0 to 12.

4. A method as claimed in claim 3 in which the homoserine lactone molecule of general formula I is N-butanoly-L-homoserine lactone (BHL) where n =0, N-dodecanoyl-L-homoserine lactone (dDHL) where n =8, or n-tetradecanoyl-L-homoserine lactone (tDHL) where n =10.

5. A method as claimed in claim 3 in which the homoserine lactone molecule of general formula II is N-(-3-oxohexanoyl)-L-homoserine lactone (OHHL) where n =2 or N-(-3-oxododecanoyl)-L-homoserine lactone (OdDHL) where n = 8.

6. A method as claimed in claim 3 in which the homoserine lactone molecule of general formula III is N-(-3-hydroxybutanoyl)-L-homoserine lactone (HBHL) where n =0.

7. A method as claimed in claim 2 in which the peptide thiolactone has a general formula (IV) as follows:

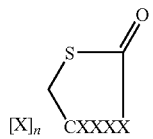

where X is any amino acid and n =1 to 10.

8. A method as claimed in claim 7 in which the peptide thiolactone molecule is:

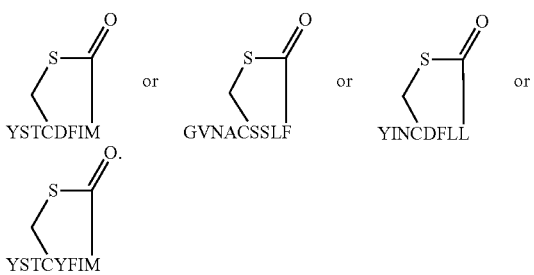

9. A method as claimed in claim 1 in which the lactone-derived signal molecule is a furanosyl borate diester.

10. A method as claimed in claim 9 in which the furanosyl borate diester is Auto Inducer-2 (AI-2),

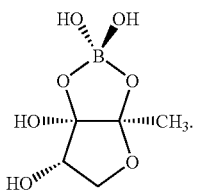

11. A method as claimed in claim 1 in which the lactone-derived signal molecule is Pro-AI-2 or a $C_1$-$C_{10}$ saturated or unsaturated carboxylic acid derivative thereof

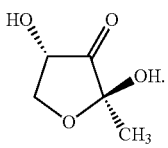

12. A method as claimed in claim 1 in which the antibody is a single chain antibody (scAb).

13. A method as claimed in claim 1 in which the antibody is an antibody fragment.

14. A method as claimed in claim 13 in which the antibody fragment is a single chain variable fragment (scFv) or a single domain fragment.

* * * * *

SEQUENCE LISTING

<160> NUMBER OF SEQ ID NOS: 11

<210> SEQ ID NO 1
<211> LENGTH: 8
<212> TYPE: PRT
<213> ORGANISM: Staphylococcus aureus
<220> FEATURE:
<221> NAME/KEY: SITE
<222> LOCATION: (4)..(8)
<223> OTHER INFORMATION: Thiolactone ring

<400> SEQUENCE: 1

Tyr Ser Thr Cys Asp Phe Ile Met
1               5

<210> SEQ ID NO 2
<211> LENGTH: 9
<212> TYPE: PRT
<213> ORGANISM: Staphylococcus aureus
<220> FEATURE:
<221> NAME/KEY: SITE
<222> LOCATION: (5)..(9)
<223> OTHER INFORMATION: Thiolactone ring

<400> SEQUENCE: 2

Gly Val Asn Ala Cys Ser Ser Leu Phe
1               5

<210> SEQ ID NO 3
<211> LENGTH: 8
<212> TYPE: PRT
<213> ORGANISM: Staphylococcus aureus
<220> FEATURE:
<221> NAME/KEY: SITE
<222> LOCATION: (4)..(8)
<223> OTHER INFORMATION: Thiolactone ring

<400> SEQUENCE: 3

Tyr Ile Asn Cys Asp Phe Leu Leu
1               5

<210> SEQ ID NO 4
<211> LENGTH: 8
<212> TYPE: PRT
<213> ORGANISM: Staphylococcus aureus
<220> FEATURE:
<221> NAME/KEY: SITE
<222> LOCATION: (4)..(8)
<223> OTHER INFORMATION: Thiolactone ring

<400> SEQUENCE: 4

Tyr Ser Thr Cys Tyr Phe Ile Met
1               5

<210> SEQ ID NO 5
<211> LENGTH: 10
<212> TYPE: PRT
<213> ORGANISM: Artificial sequence
<220> FEATURE:
<223> OTHER INFORMATION: Conventional peptide YST-1

<400> SEQUENCE: 5

Tyr Ser Thr Gly Gly Ala Gly Ser Gly Gly
1               5                   10

<210> SEQ ID NO 6
<211> LENGTH: 26

```
<212> TYPE: DNA
<213> ORGANISM: Artificial sequence
<220> FEATURE:
<223> OTHER INFORMATION: Primer

<400> SEQUENCE: 6
ggcggaggtg gctctggcgg tagtgc                                         26

<210> SEQ ID NO 7
<211> LENGTH: 17
<212> TYPE: DNA
<213> ORGANISM: Artificial sequence
<220> FEATURE:
<223> OTHER INFORMATION: Primer

<400> SEQUENCE: 7
gaattttctg tatgagg                                                   17

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
aaatacctat tgcctacggc                                                20

<210> SEQ ID NO 9
<211> LENGTH: 30
<212> TYPE: DNA
<213> ORGANISM: Artificial sequence
<220> FEATURE:
<223> OTHER INFORMATION: Primer

<400> SEQUENCE: 9
agagccacct ccgcctgaac cgcctccacc                                     30

<210> SEQ ID NO 10
<211> LENGTH: 10
<212> TYPE: PRT
<213> ORGANISM: Artificial sequence
<220> FEATURE:
<223> OTHER INFORMATION: Conventional peptide YST-2

<400> SEQUENCE: 10

Tyr Ser Thr Ala Ser Gly Gly Ala Ser Ser
1               5                   10

<210> SEQ ID NO 11
<211> LENGTH: 11
<212> TYPE: PRT
<213> ORGANISM: Artificial sequence
<220> FEATURE:
<223> OTHER INFORMATION: Peptide YST-3

<400> SEQUENCE: 11

Tyr Ser Thr Ala Gly Gly Ser Gly Ala Lys Ser
1               5                   10
```